(12) United States Patent
Kato

(10) Patent No.: US 8,401,802 B2
(45) Date of Patent: Mar. 19, 2013

(54) HAPLOTYPE ESTIMATING APPARATUS AND PROGRAM

(75) Inventor: Mamoru Kato, Yokohama (JP)

(73) Assignee: Riken, Wako-shi (JP)

( * ) Notice: Subject to any disclaimer, the term of this patent is extended or adjusted under 35 U.S.C. 154(b) by 621 days.

(21) Appl. No.: 12/597,479

(22) PCT Filed: Feb. 28, 2008

(86) PCT No.: PCT/JP2008/053567
§ 371 (c)(1),
(2), (4) Date: Oct. 23, 2009

(87) PCT Pub. No.: WO2008/136210
PCT Pub. Date: Nov. 13, 2008

(65) Prior Publication Data
US 2010/0082262 A1    Apr. 1, 2010

(30) Foreign Application Priority Data

Apr. 26, 2007  (JP) .................................. 2007-117744
Sep. 12, 2007  (JP) .................................. 2007-237139

(51) Int. Cl.
*G06F 19/00* (2011.01)
(52) U.S. Cl. ....................................................... 702/20
(58) Field of Classification Search .................... 702/20
See application file for complete search history.

(56) References Cited

FOREIGN PATENT DOCUMENTS
JP    2004-192018    7/2004

OTHER PUBLICATIONS

"Apparatus" Merriam-Webster Online, http://www.merriam-webster.com/dictionary/apparatus, last visited Jun. 13, 2012.*
Excoffier et al "Maximum-likelihood Estimation of Molecular Haplotype Frequencies in a Diploid Population", Molecular Biology and Evolution, The University of Chicago Press, US. vol. 12, 1995, pp. 921-927.
Corona et al "Identification of Deletion Polymorphisms from Haplotypes" Research in Computational Molecular Biology, Proceedings Springer-Verlag, Berlin, Germany Series, Lecture Notes in Computer Science, Apr. 21, 2007, pp. 354-365.
"Algorithms for Inferring Haplotypes" by T. Niu, Genetic Epidemiology 27 (4) 334-347 Dec. 2004.
Qin, et al. "Partition-ligation-expectation-maximaization algorithm for haplotype inference with single-nucleotide polymorphisms" Am J Hum Genet., Nov. 2002, 71 (5) 1242-1247.
Excoffier, et al. "Maximum-likelihood estimation of molecular haplotype frequencies in a diploid population" Mol Biol Evol., Sep. 1995 , 12 (5) 921-927.
Hawley, et al. "HAPLO: a program using the EM algorithm to estimate the frequencies of multi-site haplotypes" J Hered., Sep.-Oct. 1995, 86 (5) 409-411.
Ogino, et al. "New insights on the evolution of the SMN1 and SMN2 region: simulation and meta-analysis for allele and haplotype frequency calculations" European Journal of Human Genetics (2004) 12, 1015-1023.
Redon, et al. "Global variation in copy number in the human genome", vol. 444, Nov. 23, 2006. pp. 444-454.

* cited by examiner

*Primary Examiner* — Jerry Lin
(74) *Attorney, Agent, or Firm* — Brundidge & Stanger, P.C.

(57) ABSTRACT

The present invention calculates a sum of the count numbers for each of the marker sites to obtain a maximum value of the sum of the count numbers, enumerates polymorphic identification characters up to the count numbers of the polymorphic nucleotides, permutates the enumerated polymorphic identification characters so as to create any character string that has copy units of which the number equals the maximum value, divides the character string into two by the copy unit to store the divided strings as a combination of the haplotype character strings, calculates the number of identical haplotype character strings in the group, obtains a frequency of the haplotype character string in the group, and estimates the combination of the haplotype character strings (representing haplotypes) of each individual of which frequency satisfying a predetermined condition.

6 Claims, 20 Drawing Sheets

FIG.1

| | $L_1$ | | | | $L_2$ | | | | $L_3$ | | | |
|---|---|---|---|---|---|---|---|---|---|---|---|---|
| | $A_1$ | $A_2$ | $A_3$ | $A_{...}$ | $A_1$ | $A_2$ | $A_3$ | $A_{...}$ | $A_1$ | $A_2$ | $A_3$ | $A_{...}$ |
| INDIVIDUAL 1 | 1 | 1 | 0 | ... | 1 | 0 | 1 | ... | 2 | 0 | 0 | ... |
| INDIVIDUAL 2 | 0 | 2 | 0 | ... | 0 | 1 | 1 | ... | 2 | 0 | 0 | ... |
| ... | ... | ... | ... | ... | ... | ... | ... | ... | ... | ... | ... | ... |

FIG.2

| HAPLOTYPE 1 | $A_1 (L_1) A_1 (L_2) A_1 (L_3)$ |
|---|---|
| HAPLOTYPE 2 | $A_2 (L_1) A_3 (L_2) A_1 (L_3)$ |
| ... | ... |

FIG.10

| Partitioned loci 1 $L_1L_2$ | | Partitioned loci 2 $L_3L_4$ | | Ligated loci $L_1L_2L_3L_4$ | |
|---|---|---|---|---|---|
| $h_1$ | $A_1A_1$ | $h_3$ | $A_3A_3$ | $h_1h_3$ | $A_1A_1A_3A_3$ |
| $h_2$ | $A_2A_2$ | $h_4$ | $A_4A_4$ | $h_1h_4$ | $A_1A_1A_4A_4$ |
| | | | | $h_2h_3$ | $A_2A_2A_3A_3$ |
| | | | | $h_2h_4$ | $A_2A_2A_4A_4$ |

FIG.11

| Partitioned markers 1 $M_1M_2$ | | Partitioned markers 2 $M_3M_4$ | |
|---|---|---|---|
| $h_1$ | $F_1F_1$ | $h_0$ | $F_0F_0$ |
| $h_2$ | $F_{21}F_{21},F_{22}F_{22}$ | $h_4$ | $F_4F_4$ |
| $h_3$ | $F_3F_3,F_3F_3$ | $h_5$ | $F_{51}F_{51},F_{52}F_{52}$ |

| Ligated markers $M_1M_2M_3M_4$ | |
|---|---|
| $h_1h_4$ | $F_1F_1F_4F_4$ |
| $h_2h_5$ | $F_{21}F_{21}F_{51}F_{51},F_{22}F_{22}F_{52}F_{52}$ |
| $h_2h_5$ | $F_{21}F_{21}F_{52}F_{52},F_{22}F_{22}F_{51}F_{51}$ |
| $h_3h_5$ | $F_3F_3F_{51}F_{51},F_3F_3F_{52}F_{52}$ |

FIG.17

| HAPLOTYPE | PROBABILITY |
|---|---|
| $F_2F_2$ | 0.2 |
| $F_2F_1$ | 0.2 |
| $F_0F_0$ | 0.2 |
| $F_2F_2,F_2F_2$ | 0.2 |
| $F_1F_2$ | 0.2 |

FIG.18

| NUMBER OF INDIVIDUALS | $M_1$ | | $M_2$ | |
|---|---|---|---|---|
| | $F_1$ | $F_2$ | $F_1$ | $F_2$ |
| 20 | 0 | 0 | 0 | 0 |
| 47 | 0 | 1 | 0 | 1 |
| 43 | 0 | 1 | 1 | 0 |
| 52 | 0 | 2 | 0 | 2 |
| 39 | 0 | 2 | 1 | 1 |
| 15 | 0 | 2 | 2 | 0 |
| 43 | 0 | 3 | 0 | 3 |
| 49 | 0 | 3 | 1 | 2 |
| 17 | 0 | 4 | 0 | 4 |
| 35 | 1 | 0 | 0 | 1 |
| 42 | 1 | 1 | 0 | 2 |
| 43 | 1 | 1 | 1 | 1 |
| 39 | 1 | 2 | 0 | 3 |
| 16 | 2 | 0 | 0 | 2 |

FIG.19

| HAPLOTYPE | FREQUENCY |
|---|---|
| $F_2F_2$ | 0.207786 |
| $F_2F_1$ | 0.204 |
| $F_0F_0$ | 0.198608 |
| $F_2F_2,F_2F_2$ | 0.198607 |
| $F_1F_2$ | 0.191 |
| $F_2F_1,F_2F_2$ | 3.92E-07 |
| $F_1F_2,F_2F_2$ | 2.61E-07 |
| $F_2F_2,F_2F_2,F_2F_2$ | 7.16E-08 |
| $F_2F_1,F_2F_2,F_2F_2$ | 4.80E-11 |
| $F_1F_1,F_2F_2$ | 8.31E-12 |
| $F_1F_2,F_2F_1$ | 8.31E-12 |
| $F_1F_1$ | 6.17E-12 |
| $F_1F_2,F_2F_2,F_2F_2$ | 3.20E-12 |
| $F_1F_2,F_1F_2$ | 2.35E-13 |
| $F_2F_2,F_2F_2,F_2F_2,F_2F_2$ | 8.77E-14 |
| $F_2F_1,F_2F_1$ | 1.05E-14 |

FIG.22

| HAPLOTYPE | PROBABLITY |
|---|---|
| 11111111 | 0.2 |
| 11122222 | 0.2 |
| 11111111,11111111 | 0.2 |
| 11122222,11122222 | 0.2 |
| 11111111,11111111,11111111 | 0.2 |

* "1" AND "2" IN HAPLOTYPE REPRESENT $F_1$ AND $F_2$, RESPECTIVELY

FIG.23

| NUMBER OF INDIVIDUALS | $M_1$ | | $M_2$ | | $M_3$ | | $M_4$ | | $M_5$ | | $M_6$ | | $M_7$ | | $M_8$ | |
|---|---|---|---|---|---|---|---|---|---|---|---|---|---|---|---|---|
| | $F_1$ | $F_2$ | $F_1$ | $F_2$ | $F_1$ | $F_2$ | $F_1$ | $F_2$ | $F_1$ | $F_2$ | $F_1$ | $F_2$ | $F_1$ | $F_2$ | $F_1$ | $F_2$ |
| 20 | 2 | 0 | 2 | 0 | 2 | 0 | 0 | 2 | 0 | 2 | 0 | 2 | 0 | 2 | 0 | 2 |
| 38 | 2 | 0 | 2 | 0 | 2 | 0 | 1 | 1 | 1 | 1 | 1 | 1 | 1 | 1 | 1 | 1 |
| 18 | 2 | 0 | 2 | 0 | 2 | 0 | 2 | 0 | 2 | 0 | 2 | 0 | 2 | 0 | 2 | 0 |
| 37 | 3 | 0 | 3 | 0 | 3 | 0 | 0 | 3 | 0 | 3 | 0 | 3 | 0 | 3 | 0 | 3 |
| 37 | 3 | 0 | 3 | 0 | 3 | 0 | 1 | 2 | 1 | 2 | 1 | 2 | 1 | 2 | 1 | 2 |
| 44 | 3 | 0 | 3 | 0 | 3 | 0 | 2 | 1 | 2 | 1 | 2 | 1 | 2 | 1 | 2 | 1 |
| 53 | 3 | 0 | 3 | 0 | 3 | 0 | 3 | 0 | 3 | 0 | 3 | 0 | 3 | 0 | 3 | 0 |
| 17 | 4 | 0 | 4 | 0 | 4 | 0 | 0 | 4 | 0 | 4 | 0 | 4 | 0 | 4 | 0 | 4 |
| 38 | 4 | 0 | 4 | 0 | 4 | 0 | 2 | 2 | 2 | 2 | 2 | 2 | 2 | 2 | 2 | 2 |
| 40 | 4 | 0 | 4 | 0 | 4 | 0 | 3 | 1 | 3 | 1 | 3 | 1 | 3 | 1 | 3 | 1 |
| 64 | 4 | 0 | 4 | 0 | 4 | 0 | 4 | 0 | 4 | 0 | 4 | 0 | 4 | 0 | 4 | 0 |
| 47 | 5 | 0 | 5 | 0 | 5 | 0 | 3 | 2 | 3 | 2 | 3 | 2 | 3 | 2 | 3 | 2 |
| 33 | 5 | 0 | 5 | 0 | 5 | 0 | 5 | 0 | 5 | 0 | 5 | 0 | 5 | 0 | 5 | 0 |
| 14 | 6 | 0 | 6 | 0 | 6 | 0 | 6 | 0 | 6 | 0 | 6 | 0 | 6 | 0 | 6 | 0 |

FIG.24

| METHOD | CALCULATION TIME |
|---|---|
| BRUTE FORCE METHOD | 941 SECONDS |
| PL STRATEGY | 95 SECONDS |

| HAPLOTYPE | FREQUENCY BY BRUTE FORCE METHOD | FREQUENCY BY PL STRATEGY |
|---|---|---|
| 11111111,11111111 | 0.216725592 | 0.184696413 |
| 11111111 | 0.203636131 | 0.180643114 |
| 11122222 | 0.198998396 | 0.174882075 |
| 11122222,11122222 | 0.192999734 | 0.177883369 |
| 11111111,11111111,11111111,11111111 | 0.18763685 | 0.191781138 |
| 11122222,11122222,11122222 | < 0.01 | 0.018653156 |
| | < 0.01 | 0.018114592 |
| 00000000 | < 0.01 | 0.05333861 |
| ⋮ | | |

*1. IN BOTH METHODS, FREQUENCY LESS THAN 0.01 IS NOT LISTED
*2. "1", "2" AND "0" IN HAPLOTYPE REPRESENT $F_1$, $F_2$, AND $F_0$, RESPECTIVELY

FIG.25

| HAPLOTYPE | PROBABILITY |
|---|---|
| 0 | 0.25 |
| 1 | 0.25 |
| 2 | 0.25 |
| 3 | 0.25 |

FIG.26

| HAPLOTYPE | PROBABILITY |
|---|---|
| $F_0$ | 0.25 |
| $F_1$ | 0.25 |
| $F_1, F_1$ | 0.25 |
| $F_1, F_1, F_1$ | 0.25 |

FIG.27

| NUMBER OF INDIVIDUALS | IN A CNP REGION |
|---|---|
| | COPY NUMBER SUMMATION |
| 24 | 0 |
| 64 | 1 |
| 111 | 2 |
| 121 | 3 |
| 77 | 4 |
| 68 | 5 |
| 35 | 6 |

FIG.28

| NUMBER OF INDIVIDUALS | $M_1$ |
|---|---|
| | $F_1$ |
| 24 | 0 |
| 64 | 1 |
| 111 | 2 |
| 121 | 3 |
| 77 | 4 |
| 68 | 5 |
| 35 | 6 |

FIG.29

| HAPLOTYPE | FREQUENCY |
|---|---|
| $F_0$ | 0.245005 |
| $F_1$ | 0.248863 |
| $F_1, F_1$ | 0.260268 |
| $F_1, F_1, F_1$ | 0.245853 |
| $F_1, F_1, F_1, F_1$ | 1.05E-05 |
| $F_1, F_1, F_1, F_1, F_1,$ | 6.06E-12 |
| $F_1, F_1, F_1, F_1, F_1, F_1$ | 4.24E-26 |

FIG.30

| HAPLOTYPE | FREQUENCY |
|---|---|
| 0 | 0.245005 |
| 1 | 0.248863 |
| 2 | 0.260268 |
| 3 | 0.245853 |
| 4 | 1.05E-05 |
| 5 | 6.06E-12 |
| 6 | 4.24E-26 |

HAPLOTYPE ESTIMATING APPARATUS AND PROGRAM

TECHNICAL FIELD

The present invention relates to a haplotype estimating apparatus and a program, and more particularly, to a haplotype estimating apparatus and a program for effectively estimating the haplotype of the copy number polymorphism and the frequency thereof by a computer from the experimental data regarding the copy number polymorphism in consideration of the nucleotide polymorphism.

BACKGROUND ART

In order to discover a gene that causes a complex disease such as common diseases, and to realize personalized medicine, it is required to estimate a haplotype of a human individual from experimental data such as genotype data.

Conventionally, the haplotype across multiple loci is estimated from the genotype data per locus. The genotype data is independent per each locus, and the relationship across the loci (phase) is not known. FIG. 1 is an illustration of an example of the genotype data per locus. In FIG. 1, L and A represent locus and allele, respectively.

As shown in FIG. 1, the genotype data per locus has count number data of each allele in each locus in each individual. The count number data is data of a count number obtained by counting the allele in each locus in the individual. For example, in FIG. 1, the count number of an allele ($A_1$) in a locus ($L_1$) in an individual 1 is "1", and the count number of the allele ($A_1$) in a locus ($L_3$) is "2".

As explained above, the genotype data does not directly specify the phase, the relationship of alleles between the loci is unknown; in an example in FIG. 1 (for example, the individual 1), the phase between the loci $L_1$ and $L_2$ can not be specified from the count number data, and the relationship between the alleles ($A_1/A_2$) in the locus $L_1$ and the alleles ($A_1/A_3$) in the locus $L_2$ is unknown. Therefore, a method of estimating the haplotype (specifying the phase) is required.

A haplotype estimating method disclosed in Non-patent Documents 1 to 4 estimates the haplotype across the loci from the genotype data per locus. The haplotype across the loci means a combination of the alleles across the loci (combination to specify the phase). FIG. 2 is an illustration of an example of a combination of the haplotypes across the loci. In FIG. 2, A(L) represents the allele A that corresponds to the locus L.

As shown in FIG. 2, for example, it is specified that a haplotype 1 has the allele $A_1$ in the locus $L_1$, the allele $A_1$ in the locus $L_2$, and the allele $A_1$ in the locus $L_3$. In the conventional haplotype estimating method, two types of alleles are assumed in general, and the haplotype across the loci is estimated from the genotype data such as those of a single nucleotide polymorphism (abbreviated as "SNP").

There is a polymorphism referred to as a copy number polymorphism (or copy number variation, sometimes abbreviated as "CNP" in this description) other than the nucleotide polymorphism such as the SNP. FIG. 3 is an illustration of an example of the copy number polymorphism and the nucleotide polymorphism. In FIG. 3, M and F correspond to a sequence site (marker site), which is not different between individuals and identified by a label such as a fluorochrome probe, and a nucleotide (polymorphic nucleotide), which may be different between the individuals (distinguished by different fluorochromes and the like), respectively.

As shown in FIG. 3, in the copy number polymorphism, the sequence of a certain section (referred to as a "copy unit") might repeatedly appear, and there is difference in the copy number among individuals. For example, as shown in FIG. 3, in homologous chromosomes (chromosomes 1 to 4), the copy number is 1 in the chromosome 1, the copy number is 0 in the chromosome 2, the copy number is 2 in the chromosome 3, and the copy number is 3 in the chromosome 4, so that they are different to each other.

When the polymorphic nucleotide is present on the copy unit, unlike the nucleotide polymorphism in a genomic region in which the copy number polymorphism is not present, the count number of the polymorphic nucleotide depends on the copy number of two haplotypes (that is to say, diplotype) in the individual. That is to say, although the count number is basically 0, 1, or 2 (since a sexually reproducing individual has the chromosomes in pairs as the homologous chromosomes) in the nucleotide polymorphism in the genomic region in which the copy number polymorphism is not present, when there is the nucleotide polymorphism on the copy number unit, the count number of the polymorphic nucleotide varies in each individual depending on the copy number, for example, 0, 1, 2, 3, 4, 5, . . . . That is to say, the count number when there is the nucleotide polymorphism on the copy number unit does not directly link to the genotype per locus as in the conventional technique. The count number in the copy number polymorphism means the count number obtained by counting the polymorphic nucleotide associated with the marker site specified by the label on the copy unit.

Non-patent Document 5 is the haplotype estimating method for the copy number polymorphism, and is the method of estimating the haplotype across the loci by classifying the alleles into two types, which are the allele of which copy number is large and the allele of which copy number is small.

As the more general haplotype estimating method for the copy number polymorphism, there is a method of associating the copy number with the type of the allele, supposing multiple types of alleles, and estimating the haplotype across the loci.

Patent Document 1 discloses using Expectation-Maximization (EM) algorithm as the method for calculating the frequency of the haplotype.

Patent Document 1: JP-A-2004-192018

Non-Patent Document 1: Tianhua Niu "Algorithms for inferring haplotypes" Genet Epidemiol., 2004 Dec., 27(4)334-347

Non-Patent Document 2: Zhaohui S. Qin, Tianhua Niu, Jun S. Liu "Partition-ligation-expectation-maximization algorithm for haplotype inference with single-nucleotide polymorphisms" Am J Hum Genet., 2002 Nov., 71(5)1242-1247

Non-Patent Document 3: Laurent Excoffier, Montgomery Slatkin "Maximum-likelihood estimation of molecular haplotype frequencies in a diploid population" Mol Biol Evol, 1995 September., 12(5)921-927

Non-Patent Document 4: M. E. Hawley, K. K. Kidd "HAPLO: a program using the EM algorithm to estimate the frequencies of multi-site haplotypes" J Hered., 1995 September-October, 86(5)409-411

Non-Patent Document 5: Richard Redon, Shumpei Ishikawa, Karen R. Fitch, et al. "Global variation in copy number in the human genome" Nature, 2006 Nov. 23, 444(7118)444-454

DISCLOSURE OF INVENTION

Problem to be Solved by the Invention

However, conventionally, there is a problem that the method of estimating the haplotype of the copy number polymorphism and the frequency thereof by a computer from the experimental data regarding the copy number polymorphism in consideration of the nucleotide polymorphism is not developed.

That is to say, in the conventional technique, since the haplotype is estimated supposing that the individual has two chromosomes of one copy considering the copy number as the type of the allele, there is a problem that a concept of the copy number is eliminated.

In the conventional haplotype estimating method for the copy number polymorphism, since the copy number is associated with the type of the allele, there is a problem that the haplotype can not be estimated from the experimental data regarding the copy number polymorphism in consideration of the nucleotide polymorphism in principle.

There is a problem that the haplotype frequency estimating method by the EM algorithm disclosed in the Patent Document 1 can not be applied as the haplotype estimating method in consideration of the copy number polymorphism.

The present invention is made in view of the above-explained problem, and the objective thereof is to provide the haplotype estimating apparatus and the program capable of estimating the haplotype and the frequency thereof with a high degree of accuracy from the experimental data regarding the copy number polymorphism in consideration of the nucleotide polymorphism, which is not directly linked to the genotype data per locus.

Means for Solving Problems

To solve the above problems and to achieve the above objectives, according to one aspect of the present invention, a haplotype estimating apparatus that estimates a haplotype from genotype data including a copy number polymorphism and a nucleotide polymorphism of each individual in a group, includes a control unit and a storage unit, wherein the storage unit includes a count number table that stores count numbers obtained by counting polymorphic nucleotides associated with marker sites specified by a label on a copy unit of the copy number polymorphism using the genotype data for each individual, for each type of the polymorphic nucleotides, and the control unit includes a maximum value-calculating unit that calculates a sum of the count numbers for each of the marker sites based on the count numbers of the individual stored in the count number table to obtain a maximum value of the sum of the count numbers, a polymorphic identification character-enumerating unit that enumerates polymorphic identification characters associated with the type of the polymorphic nucleotides up to the number as many as the count numbers of the polymorphic nucleotides, a character string-creating unit that permutates the enumerated polymorphic identification characters so as to create any character string that has copy units of which the number equals the maximum value, a haplotype character string-storing unit that divides the character string created by the character string-creating unit into two by the copy unit to store the divided strings as a combination of the haplotype character strings, and a haplotype-estimating unit that calculates the number of identical haplotype character strings in the group, obtains a frequency of the haplotype character string in the group, and estimates the combination of the haplotype character strings, which represent haplotypes, of each individual of which frequency satisfying a predetermined condition.

According to another aspect of the present invention, in the haplotype estimating apparatus, the haplotype-estimating unit calculates the frequency of the haplotype character string based on the Hardy-Weinberg Principle, and uses a Hardy-Weinberg equilibrium in the group as the predetermined condition.

According to still another aspect of the present invention, in the haplotype estimating apparatus, the polymorphic identification character-enumerating unit enumerates the polymorphic identification character indicating a nucleotide deletion as a type of the polymorphic nucleotide up to the number as many as the number obtained by subtracting the sum from the maximum value.

According to still another aspect of the present invention, in the haplotype estimating apparatus, the character string-creating unit confirms that the number of the polymorphic identification characters in the created character string and the count number of the polymorphic nucleotide for each type in the count number table conform to each other, and eliminates the character string when they are not conform to each other.

According to still another aspect of the present invention, in the haplotype estimating apparatus, the control unit includes a partitioning unit that partitions the copy unit into multiple partitions by a unit of the marker sites, and, for the nucleotide polymorphism of the marker sites included in the partition, controls the maximum value-calculating unit, the polymorphic identification character-enumerating unit, the character string-creating unit, the haplotype character string-storing unit, and the haplotype-estimating unit to execute the process for each of the partitions, and a ligating unit that reproduces the haplotype character string composed of the partitions by ligating each of the partitions on the copy unit with each other between the haplotype character strings having same repeat pattern of the copy unit, for the haplotype character string estimated by the haplotype-estimating unit for each of the partitions.

According to still another aspect of the present invention, in the haplotype estimating apparatus, the haplotype-estimating unit further includes a haplotype frequency-calculating unit that repeats an M step of calculating the frequency of the haplotype character string in the group by weighting with the frequency of the combination having the haplotype character string as one of them, and an E step of obtaining the frequency of the combination by a product of the frequency of the haplotype character strings composing the combination to calculate the weight based on the frequencies of the combination until a value of the frequency converges, using an expectation-maximization (EM) algorithm.

According to still another aspect of the present invention, in the haplotype estimating apparatus, wherein, at the M step, the frequency of the haplotype character string is calculated based on a following mathematical expression 1

$$P(h_i) = \frac{\sum_j \sum_k N(c_j) \cdot \delta(h_j, d_{jk}) \cdot w_{jk}}{2n} \quad \text{(Expression 1)}$$

(wherein $P(h_i)$ represents the frequency of the haplotype character string, h represents the haplotype character string, and i represents an index of the haplotype character string. Also, n represents the number of the individuals composing the group, j represents an index of a pattern of the count number in the count number table, k is an index of the combination of the haplotype character string, and $N(c_j)$ represents the number of the individuals having a pattern j of the count number. Also, $\delta(h_i, d_{jk})$ is a function to return 1 when a combination $d_{jk}$ of the haplotype character strings has the haplotype character string $h_i$ on one side, return 2 when this has the haplotype character string on both sides, and return 0 when this does not have the haplotype character string $h_i$, and d represents the combination of the haplotype character strings. Also, $w_k$ is the weight by the frequency of the combination of the haplotype character strings), and, at the E step, the frequency of the combination of the haplotype character strings is obtained based on a following mathematical expression 2, and the weight is calculated by dividing the frequency of the combination of the haplotype character strings by a sum total of the frequency of the combination in the group $$P(d_{jk}) = P(h_1 \oplus h_m) = \begin{cases} P(h_1)P(h_m) & \text{if } 1 = m \\ 2P(h_1)P(h_m) & \text{if } 1 \neq m \end{cases} \quad \text{(Expression 2)}$$

(wherein, $P(d_{jk})$ represents the frequency of the combination of the haplotype character strings. Also, $h_l$ and $h_m$ represent two haplotype character strings composing the combination, and $P(h_l)$ and $P(h_m)$ represent the frequencies of the two haplotype character strings, respectively.)

According to still another aspect of the present invention, in the haplotype estimating apparatus, the storage unit further includes a copy number summation storage unit that stores a copy number summation of the copy number polymorphism in each individual, and the control unit further includes a count number table-creating unit that creates the count number table in which the copy number summation in each individual stored in the copy number summation storage unit is regarded as the count number of any one of the polymorphic nucleotides, and a copy number-setting unit that calculates the number of the polymorphic identification characters associated with the one polymorphic nucleotide in the haplotype character string in the combination of the haplotypes estimated by the haplotype-estimating unit and sets the calculated number as the copy number in the haplotype.

According to still another aspect of the present invention, in the haplotype estimating apparatus, the haplotype frequency-calculating unit obtains the log likelihood difference between the frequency of the haplotype character string calculated at the M step and the frequency of the haplotype character string calculated at the previous M step, and judges that the value of the frequency converges when the log likelihood difference is equal to or smaller than the predetermined threshold.

According to still another aspect of the present invention, a program makes a haplotype estimating apparatus including a control unit and a storage unit execute a haplotype estimating method, the apparatus estimating a haplotype from genotype data including a copy number polymorphism and a nucleotide polymorphism of each individual in a group, wherein the storage unit includes a count number table that stores count numbers obtained by counting polymorphic nucleotides associated with marker sites specified by a label on a copy unit of the copy number polymorphism using the genotype data for each individual, for each type of the polymorphic nucleotides, and the method, executed by the control unit, includes a maximum value calculating step of calculating a sum of the count numbers for each of the marker sites based on the count numbers of the individual stored in the count number table to obtain a maximum value of the sum of the count numbers, a polymorphic identification character enumerating step of enumerating polymorphic identification characters associated with the type of the polymorphic nucleotides up to the number as many as the count numbers of the polymorphic nucleotides, a character string creating step of permutating the enumerated polymorphic identification characters so as to create any character string that has copy units of which the number equals the maximum value, a haplotype character string storing step of dividing the character string created at the character string creating step into two by the copy unit to store the divided strings as a combination of the haplotype character strings, and a haplotype estimating step of calculating the number of identical haplotype character strings in the group, obtaining a frequency of the haplotype character string in the group, and estimating the combination of the haplotype character strings, which represent haplotypes, of each individual of which frequency satisfying a predetermined condition.

According to still another aspect of the present invention, a haplotype estimating method is executed by a haplotype estimating apparatus that estimates a haplotype from genotype data including a copy number polymorphism and a nucleotide polymorphism of each individual in a group, including a control unit and a storage unit, wherein the storage unit includes a count number table that stores count numbers obtained by counting polymorphic nucleotides associated with marker sites specified by a label on a copy unit of the copy number polymorphism using the genotype data for each individual, for each type of the polymorphic nucleotides, and the method, executed by the control unit, includes a maximum value calculating step of calculating a sum of the count numbers for each of the marker sites based on the count numbers of the individual stored in the count number table to obtain a maximum value of the sum of the count numbers, a polymorphic identification character enumerating step of enumerating polymorphic identification characters associated with the type of the polymorphic nucleotides up to the number as many as the count numbers of the polymorphic nucleotides, a character string creating step of permutating the enumerated polymorphic identification characters so as to create any character string that has copy units of which the number equals the maximum value, a haplotype character string storing step of dividing the character string created at the character string creating step into two by the copy unit to store the divided strings as a combination of the haplotype character strings, and a haplotype estimating step of calculating the number of identical haplotype character strings in the group, obtaining a frequency of the haplotype character string in the group, and estimating the combination of the haplotype character strings, which represent haplotypes, of each individual of which frequency satisfying a predetermined condition.

According to still another aspect of the present invention, at the haplotype estimating step in the haplotype estimating method, the frequency of the haplotype character string is calculated based on the Hardy-Weinberg Principle, and a Hardy-Weinberg equilibrium in the group is used as the predetermined condition.

According to still another aspect of the present invention, at the polymorphic identification character enumerating step in the haplotype estimating method, the polymorphic identification character indicating a nucleotide deletion is enumerated as a type of the polymorphic nucleotide up to the number as many as the number obtained by subtracting the sum from the maximum value.

According to still another aspect of the present invention, at the character string creating step in the haplotype estimating method, it is confirmed that the number of the polymorphic identification characters in the created character string and the count number of the polymorphic nucleotide for each type in the count number table conform to each other, and the character string is eliminated when they are not conform to each other.

According to still another aspect of the present invention, the haplotype estimating method, executed by the control unit, includes a partition step of partitioning the copy unit into multiple partitions by a unit of the marker sites, and, for the nucleotide polymorphism of the marker sites included in the partition, controlling the maximum value calculating step, the polymorphic identification character enumerating step, the character string creating step, the haplotype character string storing step, and the haplotype estimating step to execute the process for each of the partitions, and a ligation step of reproducing the haplotype character string composed of the partitions by ligating each of the partitions on the copy unit with each other between the haplotype character strings having same repeat pattern of the copy unit, for the haplotype character string estimated at the haplotype estimating step for each of the partitions.

According to still another aspect of the present invention, in the haplotype estimating method, the haplotype estimating step further includes a haplotype frequency calculating step of repeating an M step of calculating the frequency of the haplotype character string in the group by weighting with the frequency of the combination having the haplotype character string as one of them, and an E step of obtaining the frequency of the combination by a product of the frequency of the haplotype character strings composing the combination to calculate the weight based on the frequencies of the combination until a value of the frequency converges, using an expectation-maximization (EM) algorithm.

According to still another aspect of the present invention, at the M step in the haplotype estimating method, the frequency of the haplotype character string is calculated based on a following mathematical expression 1

$$P(h_i) = \frac{\sum_j \sum_k N(c_j) \cdot \delta(h_j, d_{jk}) \cdot w_{jk}}{2n}$$ (Expression 1)

(wherein $P(h_i)$ represents the frequency of the haplotype character string, h represents the haplotype character string, and i represents an index of the haplotype character string. Also, n represents the number of the individuals composing the group, j represents an index of a pattern of the count number in the count number table, k is an index of the combination of the haplotype character string, and $N(c_j)$ represents the number of the individuals having a pattern j of the count number. Also, $\delta(h_i, d_{jk})$ is a function to return 1 when a combination $d_{jk}$ of the haplotype character strings has the haplotype character string $h_i$ on one side, return 2 when this has the haplotype character string $h_i$ on both sides, and return 0 when this does not have the haplotype character string $h_i$, and d represents the combination of the haplotype character strings. Also, $w_{jk}$ is the weight by the frequency of the combination of the haplotype character strings), and, at the E step, the frequency of the combination of the haplotype character strings is obtained based on a following mathematical expression 2, and the weight is calculated by dividing the frequency of the combination of the haplotype character strings by a sum total of the frequency of the combination in the group $$P(d_{jk}) = P(h_1 \oplus h_m) = \begin{cases} P(h_1)P(h_m) & \text{if } 1 = m \\ 2P(h_1)P(h_m) & \text{if } 1 \neq m \end{cases}$$ (Expression 2)

(wherein, $P(d_{jk})$ represents the frequency of the combination of the haplotype character strings. Also, $h_i$ and $h_m$ represent two haplotype character strings composing the combination, and $P(h_i)$ and $P(h_m)$ represent the frequencies of the two haplotype character strings, respectively.)

According to still another aspect of the present invention, in the haplotype estimating method, the storage unit further includes a copy number summation storage unit that stores a copy number summation of the copy number polymorphism in each individual, and the method, executed by the control unit, further includes a count number table creating step of creating the count number table in which the copy number summation in each individual stored in the copy number summation storage unit is regarded as the count number of any one of the polymorphic nucleotides, and a copy number setting step of calculating the number of the polymorphic identification characters associated with the one polymorphic nucleotide in the haplotype character string in the combination of the haplotypes estimated at the haplotype estimating step and setting the calculated number as the copy number in the haplotype.

According to still another aspect of the present invention, at the haplotype frequency calculating step in the haplotype estimating method, the log likelihood difference is obtained between the frequency of the haplotype character string calculated at the M step and the frequency of the haplotype character string calculated at the previous M step, and it is judged that the value of the frequency converges when the log likelihood difference is equal to or smaller than the predetermined threshold.

Effect of the Invention

According to the present invention, the haplotype and the frequency thereof can be estimated with a high degree of accuracy from the experimental data regarding the copy number polymorphism in consideration of the nucleotide polymorphism, which is not directly linked to the genotype data per locus.

According to the present invention, even when the count number is different in each marker site, the process is performed regarding that deficient count number is a result of the nucleotide deletion, so that highly accurate haplotype estimating apparatus can be provided in consideration of the polymorphism of the nucleotide deletion, which may not be experimentally detected.

According to the present invention, since it is verified whether an estimation result of a possible combination of the haplotype character strings by the character string conforms to the experimental data, so that the possible combination of the haplotypes can be generated with a high degree of accuracy.

According to the present invention, a result of process performed by partitioning the copy unit into multiple partitions is integrated using a Partition-Ligation strategy (PL strategy), so that calculation time can be reduced even when the number of possible haplotypes, which may be taken, when the number of marker sites increases drastically increases.

According to the present invention, likelihood of the haplotype can be evaluated with a high degree of accuracy using the EM algorithm.

According to the present invention, the copy number in the haplotype and the frequency thereof can be estimated with a high degree of accuracy using the copy number summation data of the copy number polymorphism in the individual.

BRIEF DESCRIPTION OF THE DRAWINGS

FIG. 1 is an illustration of an example of the genotype data per locus;

FIG. 2 is an illustration of an example of a combination of the haplotypes across the loci;

FIG. 10 is an illustration of an example of ligation process in the PL strategy in the haplotype estimating method, which does not take the copy number polymorphism into consideration;

FIG. 11 is an illustration of an example of the ligation process in the PL strategy of the haplotype estimating method in consideration of the copy number polymorphism according to this embodiment;

FIG. 17 is a data diagram showing an example of the result of the haplotype estimation for being read;

FIG. 18 is an illustration of the output count number data as a result of reading data of the haplotypes and the probabilities thereof in the number of individuals, 500;

FIG. 19 is an illustration of the output result of the haplotypes and the frequencies thereof according to the haplotype estimating apparatus 100;

FIG. 22 is an illustration of an example of the haplotypes and the frequencies thereof used in the simulation experiment;

FIG. 23 is an illustration of count number data of the 500 individuals created for the read haplotypes and the probabilities thereof;

FIG. 24 is an illustration showing a result of application of the example;

FIG. 25 is an illustration of the copy numbers (the number of copy units) present in the haplotypes and the probabilities of the haplotypes set in this example;

FIG. 26 is an illustration representing the copy numbers shown in FIG. 25 as the count numbers of the provisional nucleotide $F_1$;

FIG. 27 is an illustration of the summation of the copy numbers in each individual drawn;

FIG. 28 is an illustration representing the summation of the copy numbers shown in FIG. 27 as the count numbers of the provisional nucleotide $F_1$;

FIG. 29 is an illustration of the haplotype character strings and the frequencies thereof estimated by the haplotype estimating apparatus 100; and FIG. 30 is an illustration of the haplotypes of each copy number and the frequencies thereof calculated from the estimated haplotype character strings.

Figures 3, 4:
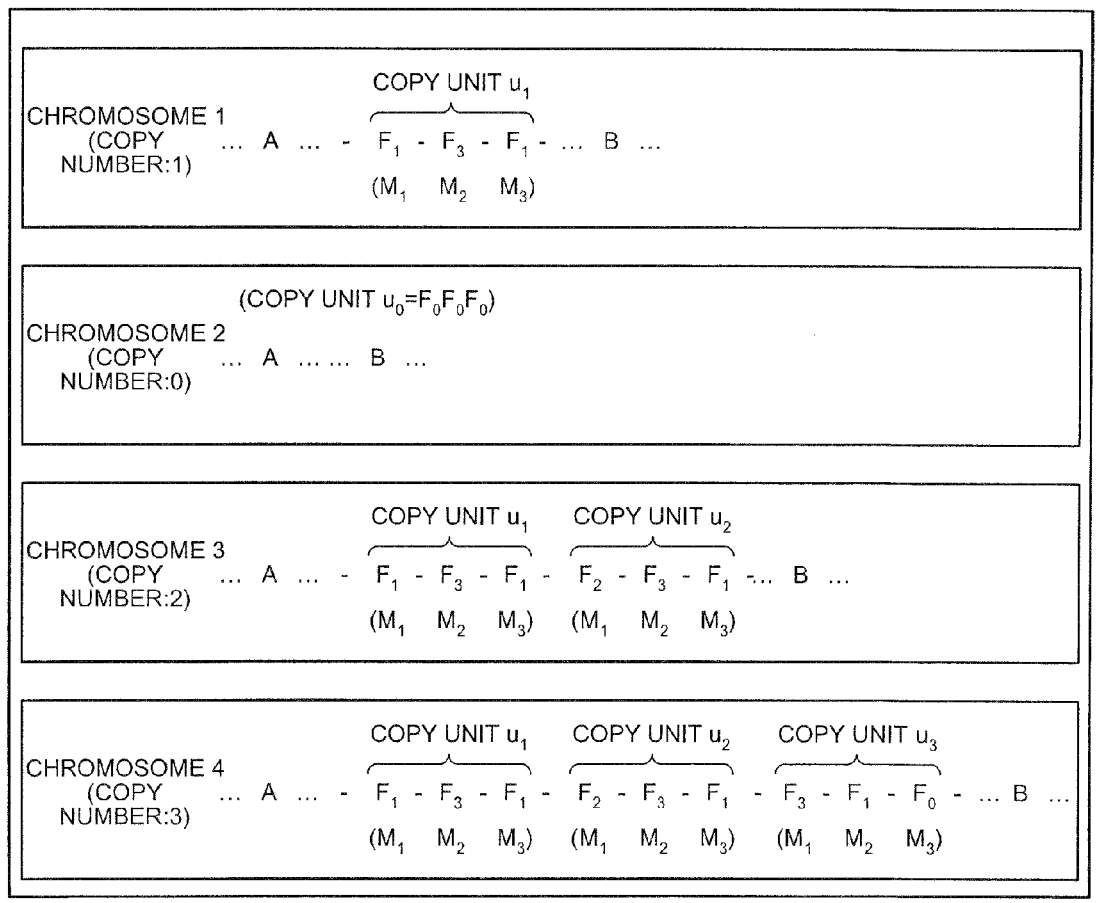
FIG. 3 is an illustration of an example of the copy number polymorphism and the nucleotide polymorphism.
FIG. 4 is an illustration of an example of experimental data of the copy number polymorphism in consideration of the nucleotide polymorphism.

EXPLANATIONS OF LETTERS OF NUMERALS 100 haplotype estimating apparatus
102 control unit
102a maximum value-calculating unit
102b polymorphic identification character-enumerating unit
102c character string-creating unit
102d haplotype character string-storing unit
102e haplotype-estimating unit
102f haplotype frequency-calculating unit
102g partitioning unit
102h ligating unit
102j count number table-creating unit
102k copy number-setting unit
104 communication control interface unit
106 storage unit
106a count number table
106b haplotype character string file
106c genotype data file
106d copy number summation file
108 input/output control interface unit
112 input device
114 output device
200 external system
300 network Best Modes for Carrying Out the Invention Embodiments of a haplotype estimating apparatus, a haplotype estimating method, a program, and a recording medium therefore according to the present invention will be explained below in detail with reference to the accompanying drawings. The invention is not limited to the embodiments.

Overview of Present Invention

Hereinafter, an overview of the present invention is explained, and thereafter, a configuration, a process and the like of the present invention are explained in detail. First, difference in haplotype estimation between cases with a copy number polymorphism and without the copy number polymorphism is present is explained.

In a nucleotide polymorphism on a genomic region without the copy number polymorphism, a count number is basically 0, 1 or 2. That is to say, in an example in FIG. 3, this is when haplotypes of all individuals do not have the copy number other than one like a chromosome 1. That is to say, in the nucleotide polymorphism on the genomic region without the copy number polymorphism, when summing up the count numbers of each different type of the polymorphic nucleotides in each marker site, a total number is necessarily 2.

In an example of having two chromosomes 1 in FIG. 3, for example, the haplotype is represented as [$F_1(M_1)F_3(M_2)F_1(M_3)/F_1(M_1)F_3(M_2)F_1(M_3)$] (two homologous chromosomes are separated from each other with "/". Hereinafter, marker position indication with (M) is omitted, and the polymorphic nucleotides [$F_1/F_1$], [$F_3/F_3$], and [$F_1/F_1$] correspond to $M_1$, $M_2$, and $M_3$, respectively (directly linked to a genotype per locus). That is to say, the count numbers of each nucleotide in each marker site are experimentally identified as $F_1$, $F_2$, $F_3$ are 2, 0, 0, in $M_1$, 0, 0, 2 in $M_2$ and 2, 0, 0 in $M_3$, respectively, and the total number is 2 in every marker site (2+0+0 in $M_1$, 0+0+2 in $M_2$, and 2+0+0 in $M_3$).

On the other hand, when the polymorphic nucleotide is present on the copy unit, the number of copy units located on one chromosome might be other than one, so that the total number of the count numbers of each nucleotide in each marker site might be other than two, unlike in the above explanation. That is to say, a sum of the count numbers depends on the copy numbers of two haplotypes in the individual, and varies in each individual so as to depend on the copy number, for example, 0, 1, 2, 3, 4, 5, . . . . Therefore, the count number when the nucleotide polymorphism is present on the copy number unit is not directly linked to the genotype per locus as in the conventional art, so that an idea is required to estimate the haplotype.

For example, in the individual having the chromosomes 1 and 3 in FIG. 3 as the homologous chromosomes, [$F_1F_3F_1/F_1F_3F_1$, $F_2F_3F_1$] (copy units are separated from each other with ",") is located on the homologous chromosomes, and [$F_1/F_1$, $F_2$], [$F_3/F_3$, $F_3$], and [$F_1/F_1$, $F_1$] correspond to $M_1$, $M_2$, and $M_3$, respectively. The count numbers of each nucleotide in each marker site are experimentally identified as $F_1$, $F_2$, $F_3$ are 2, 1, 0, in $M_1$, 0 0, 3 in $M_2$, and 3, 0, 0 in $M_3$, respectively, and the total number is 3 in each marker site (2+1+0 in $M_1$, 0+0+3 in $M_2$, and 3+0+0 in $M_3$) to conform to the sum of the copy numbers of the haplotypes.

When having the chromosomes 1 and 2 in FIG. 3, it becomes [$F_1F_3F_1/F_0F_0F_0$] ($F_0$ represents deletion, and the nucleotide may not be experimentally identified), and [$F_1/F_0$], [$F_3/F_0$], and [$F_1/F_0$] correspond to $M_1$, $M_2$, and $M_3$, respectively. $F_1$, $F_2$ and $F_3$ are identified as 1, 0, 0 in $M_1$, 0, 0, 1 in $M_2$, and 1, 0, 0 in $M_3$, respectively, and the total number is 1 in each marker site to conform to the copy number of the haplotype.

FIG. 4 is an illustration of an example of copy number data obtained from experimental data of the copy number polymorphism in consideration of the nucleotide polymorphism. M corresponds to a sequence site (marker site), which is not different between the individuals, identified by a label such as a fluorochrome probe, and F corresponds to the nucleotide (polymorphic nucleotide), which may be different between the individuals, (distinguished by different fluorochromes and the like), respectively.

In FIG. 4, in an individual 1, 2+1+0 in $M_1$, 1+1+1 in $M_2$, and 2+0+1 in $M_3$, so that the total number is 3, and it may be predicted that the sum of the copy numbers is 3 from the above-explained characteristics. On the other hand, in an individual 2, 0+0+0 in $M_1$, 0+3+0 in $M_2$, and 2+2+0 in $M_3$, so that they are different from each other; however, in consideration of presence of nucleotide deletion, it is considered that the sum of the copy numbers is 4 (it is predicted that four nucleotides are deleted in $M_1$, and one nucleotide is deleted in $M_2$).

Figure 5:
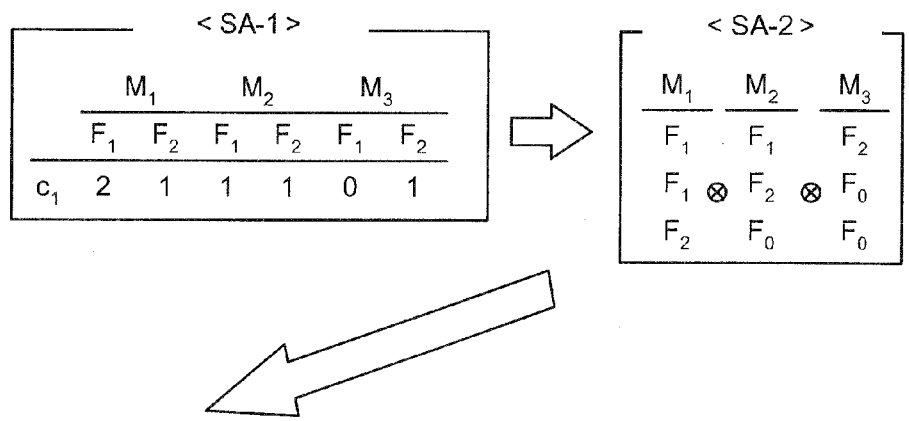
FIG. 5 is a flow diagram showing overview of the present invention.

Summarizing the above-explanation, the experimental data regarding the copy number polymorphism in consideration of the polymorphic nucleotide includes the count number data in which the count numbers of the polymorphic nucleotide experimentally identified by the label such as the fluorochrome probe is recorded. Although the count number data is not directly linked to the genotype data per locus unlike the nucleotide polymorphism on the genomic region without the copy number polymorphism, the total number of the count numbers conforms to the sum of the copy numbers of the two haplotypes (except a case of the nucleotide deletion). The present invention is to estimate the haplotype from the experimental data regarding the copy number polymorphism in consideration of the nucleotide polymorphism using the characteristics. That is to say, in order to estimate the haplotype and frequency thereof from the count number data obtained by counting the polymorphic nucleotides, the present invention finds a diplotype (a combination of the haplotypes) consistent with the count number data, and calculates the frequency of the haplotype using the count number data. Herein, "consistent" is intended to mean that the count numbers of each polymorphic nucleotide in each marker site counted from the diplotype conform to the count numbers of each nucleotide in each marker site in the count number data. When the diplotype consistent with the count number data may be found, the frequency of the haplotype may be calculated from the count number data using the Expectation-Maximization (EM) algorithm and the Gibbs sampling method. Overview of the present invention will be explained below in association with the symbols used in the above-mentioned explanation of each of the figures. FIG. 5 is a flow diagram showing overview of the present invention.

The present invention relates to a haplotype estimating apparatus that estimates a haplotype from genotype data including a copy number polymorphism and a nucleotide polymorphism of each individual in a group, including a control unit and a storage unit, a haplotype estimating method executed by the haplotype estimating apparatus, and a program therefore.

The haplotype estimating apparatus includes a count number table that stores count numbers ($c_1$) obtained by counting polymorphic nucleotides (F) associated with marker sites (M) specified by a label on a copy unit (u) of the copy number polymorphism for each individual (individual 1, individual 2, . . . ), for each type of the polymorphic nucleotides ($F_1$, $F_2$,). The haplotype estimating apparatus may create the count number table in which a copy number summation of the copy number polymorphism in each individual stored in the storage unit is regarded as the count number of any one of the polymorphic nucleotides. FIG. 5 <SA-1> depicts an example of the count number table showing the count numbers for an individual.

The haplotype estimating apparatus calculates a sum (2+1, 1+1, 0+1) of the count numbers for each of the marker sites ($M_1$, $M_2$, $M_3$) based on the count numbers ($c_1$) of the individual (for example, individual 1) stored in the count number table to obtain a maximum value (3 in this case) of the sum of the count numbers.

The haplotype estimating apparatus enumerates polymorphic identification characters (for example, $F_1$, $F_2$) associated with the type of the polymorphic nucleotides up to the number as many as the count numbers of the polymorphic nucleotides (for example, two of $F_1$ associated with $M_1$). See FIG. 5 <SA-2>. As shown in FIG. 5 <SA-2>, the haplotype estimating apparatus enumerates the polymorphic identification character ($F_0$) indicating a nucleotide deletion as a type of the polymorphic nucleotide up to the number as many as the number obtained by subtracting the sum from the maximum value (for example, 3−2=1 regarding $M_2$).

As shown in FIG. 5 <SA-3 to 4>, the haplotype estimating apparatus permutates the enumerated polymorphic identification characters so as to create any character string (see <SA-4>) in which the copy unit is repeated up to the number of times as many as the maximum value (three times in this case).

That is to say, as an example, the haplotype estimating apparatus first draws a group of polymorphic identification characters enumerated for each marker site (M) as many as the number of the copy units (u) to make all possible combinations, thereby creating character strings of a copy unit (u), as shown in FIG. 5 (SA-3). In order to create every character string in which the copy unit is repeated up to the same number of times as the maximum value, a set of character strings of the copy unit (u) is created by arbitrarily combining the created character strings of the copy unit (u) (individual character string separated by "," is the character string of the copy unit, and an entire character string enclosed by { } is the set of the character strings of the copy unit in SA-4). Then, the haplotype estimating apparatus confirms that the number of the polymorphic identification characters in the created character string (the created set of the character strings of the copy unit) and the count number of the polymorphic nucleotide for each type in the count number table conform to each other, and eliminates the character string when they are not conform to each other (SA-5).

Figure 6:
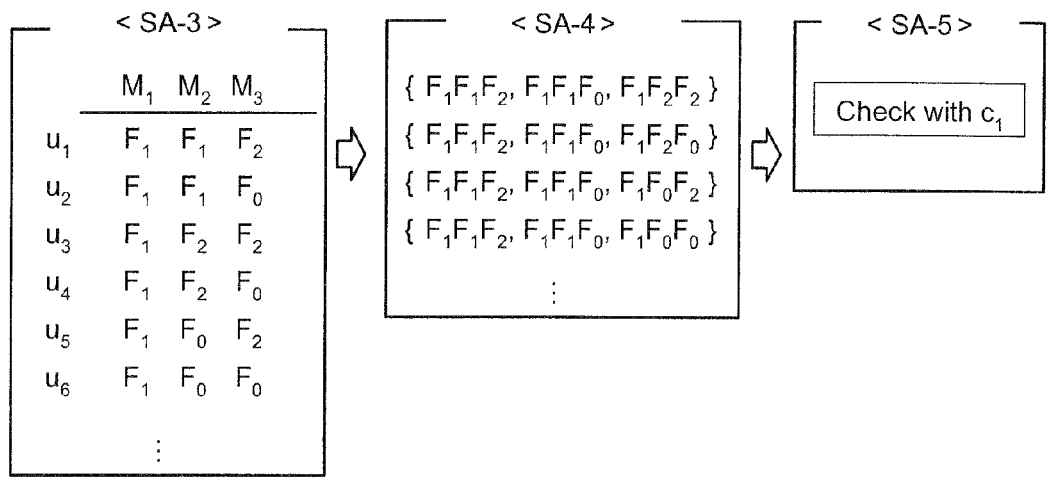
FIG. 6 is an illustration of an example of a haplotype representational form according to the present invention.

The haplotype estimating apparatus divides the created character string into any two character strings (hereinafter, "haplotype character string") by the copy unit to store the divided strings as a combination of the haplotype character strings. For example, when separating the character string $[F_1F_1F_2, F_1F_1F_0, F_1F_1F_2]$ on the uppermost stage of <SA-4> in FIG. 5, four combinations of the haplotype character strings, which are $[/F_1F_1F_2, F_1F_1F_0, F_1F_1F_2]$, $[F_1F_1F_2/F_1F_1F_0, F_1F_1F_2]$, $[F_1F_1F_2, F_1F_1F_0/F_1F_1F_2]$, and $[F_1F_1F_2, F_1F_1F_0, F_1F_1F_2/]$ may be created. For example, the character strings on both sides of "/" (slash) in $[F_1F_3F_1/F_1F_3F_1, F_2F_3F_1]$ represent two possible haplotypes in each individual such as $[F_1F_3F_1]$ and $[F_1F_3F_1, F_2F_3F_1]$. That is to say, the character string represented in pairs (such as $[F_1F_3F_1/F_1F_3F_1, F_2F_3F_1]$ represents a pair of haplotypes and also represents the diplotype (haplotype/haplotype) at the same time. FIG. 6 is an illustration of an example of a haplotype representational form output by the present invention.

As shown in FIG. 6, the haplotype representational form represents the nucleotide polymorphism and the copy number polymorphism at the same time. That is to say, unlike the haplotype representational form in the conventional method, which does not take the copy number polymorphism into consideration (refer to FIG. 2), the haplotype representation form of the present invention, which treats both of the copy number polymorphism and the nucleotide polymorphism is represented by the copy unit as shown in FIG. 6.

The haplotype estimating apparatus calculates the number of identical haplotype character strings in the group, obtains a frequency of the haplotype character string in the group, and estimates the combination of the haplotype character strings (representing haplotypes) of each individual of which frequency satisfying a predetermined condition. The haplotype estimating apparatus may calculate the frequency based on the Hardy-Weinberg Principle, and determine that the frequency is satisfied with the predetermined condition when the frequency in the group is held in a Hardy-Weinberg equilibrium.

The haplotype estimating apparatus may partition the copy unit (u) into multiple partitions by a unit of the marker sites (M), and, for the nucleotide polymorphism of the marker sites included in the partition, control the calculation of the maximum value, the enumeration of the polymorphic identification character, the creation of the character string, the storage of the haplotype character string, and the estimation of the haplotype, which are aforementioned, to execute the process for each of the partitions.

In this case, the haplotype estimating apparatus reproduces the haplotype character string composed of the partitions by ligating each of the partitions on the copy unit with each other between the haplotype character strings having same repeat pattern of the copy unit, for the haplotype character string calculated for each of the partitions. This allows calculation time to be reduced.

The haplotype estimating apparatus may repeat an M step of calculating the frequency of the haplotype character string in the group by weighting with the frequency of the combination having the haplotype character string as one of them, and an E step of obtaining the frequency of the combination by a product of the frequency of the haplotype character strings composing the combination to calculate the weight based on the frequencies of the combination until a value of the frequency converges, using an expectation-maximization (EM) algorithm, in order to calculate the frequency satisfying the predetermined condition. A detailed explanation of processing using the EM algorithm will be described later. When using the count number table in which the copy number summation in each individual is regarded as the count number of any one of the polymorphic nucleotides, the haplotype estimating apparatus may calculate the number of the polymorphic identification characters associated with the one polymorphic nucleotide in the haplotype character string in the estimated combination of the haplotypes, and set the calculated number as the copy number in the haplotype. This is the overview of the present invention.

Configuration of Haplotype Estimating Apparatus

Figure 7:
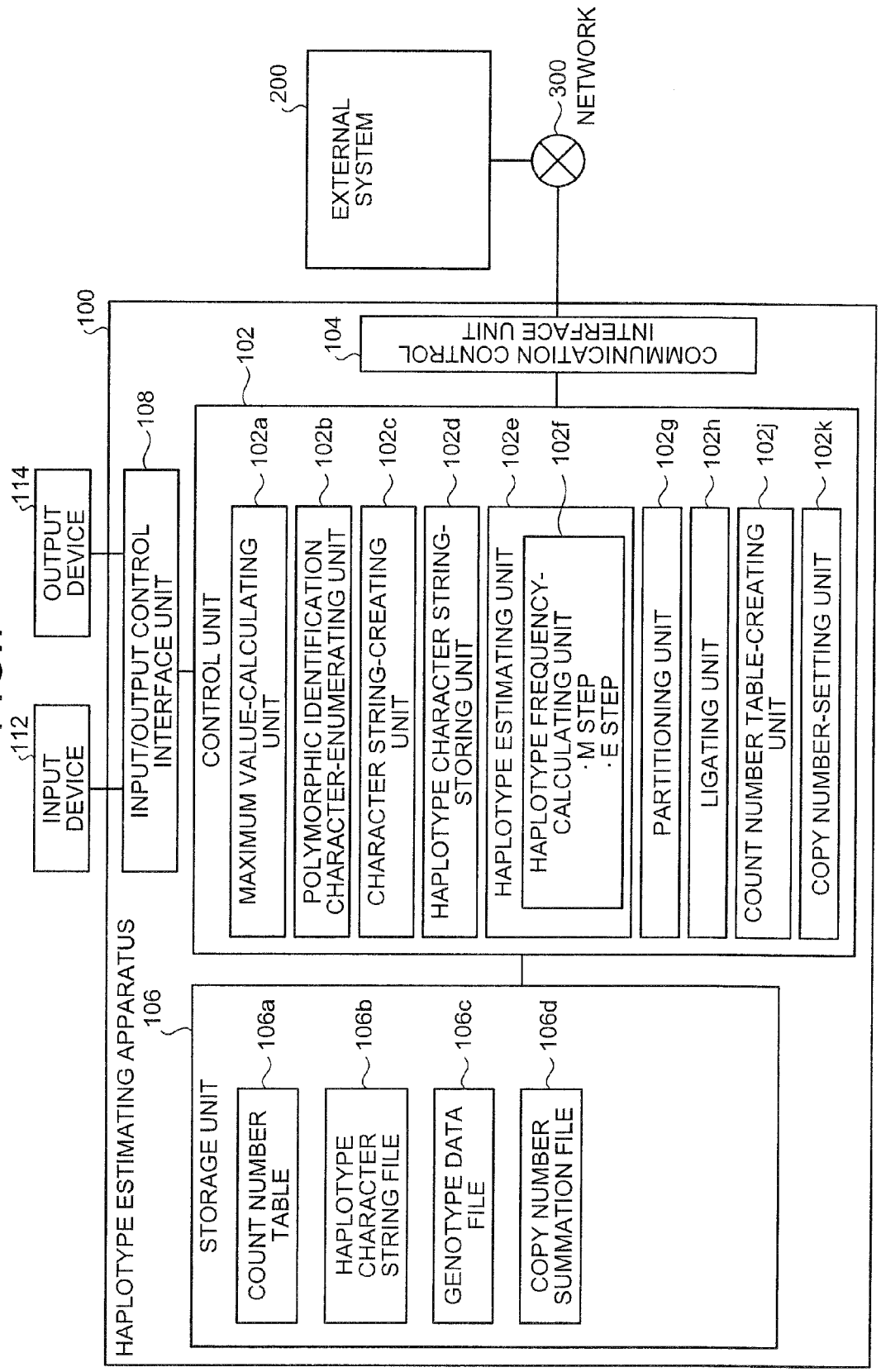
FIG. 7 is a block diagram showing an example of a configuration of the haplotype estimating apparatus to which the present invention is applied.

First, a configuration of a haplotype estimating apparatus will be explained below. FIG. 7 is a block diagram showing an example of a configuration of the haplotype estimating apparatus to which the present invention is applied. FIG. 7 schematically depicts only a part related to the present invention in the configuration.

In FIG. 7, the haplotype estimating apparatus 100 schematically includes a control unit 102 such as a CPU which integrally controls the entire operation of the haplotype estimating apparatus 100, a communication control interface unit 104 connected to a communication device (not shown) such as a router connected to a communication line or the like, an input/output control interface unit 108 connected to an input device 112 or an output device 114, and a storage unit 106 that stores various databases or tables. These components are communicably connected through an arbitrary communication path.

The various databases or tables (count number table 106a to copy number summation file 106d) stored in the storage unit 106 are storage means such as a fixed disk device or the like, and store various programs, tables, files, databases, web pages, and the like which are used in various processes.

Of these constituent elements of the storage unit 106, the count number table 106a stores count numbers obtained by counting polymorphic nucleotides associated with marker sites specified by a label on a copy unit of the copy number polymorphism using the genotype data for each individual, for each type of the polymorphic nucleotides. As described above, FIG. 4 and FIG. 5 <SA-1> depict an example of count number data stored in the count number table 106a. As shown in FIG. 4, information stored in the count number table 106a defines a count number for each individual, for each of the marker sites, and for each type of the polymorphic nucleotides.

The haplotype character string file 106b stores a possible combination of the haplotype character string's, calculated based on the count number data of the individual stored in the count number table 106a. For example, the haplotype character string file 106b stores the haplotype character strings in the haplotype representational form shown in FIG. 6.

The genotype data file 106c stores genotype data including a copy number polymorphism and a nucleotide polymorphism of each individual in a group. The genotype data file 106c may store the experimental data (such as the experimental data by a DNA chip, PCR and the like) indicating the polymorphic nucleotide associated with the marker site specified by the label on the copy unit of the copy number polymorphism. As the label, the probe identifiable by pigment without a fluorescence property, a radioisotope, protein such as GFP and GRP, a His tag, biotinylation and the like may be used other than the fluorescent probe.

The copy number summation file 106d stores a copy number summation of the copy number polymorphism (the summation of the numbers of the copy units across the two homologous chromosomes) in each individual.

In FIG. 7, the communication control interface unit 104 performs communication control between the haplotype estimating apparatus 100 and the network 300 (or a communication device such as a router). More specifically, the communication control interface unit 104 has a function of performing data communication with another terminal through a communication line.

In FIG. 7, the input/output control interface unit 108 controls the input device 112 and the output device 114. As the output device 114, not only a monitor (including a household-use television) but also a speaker may be used. As the input device 112, a keyboard, a mouse, a microphone or the like may be used.

In FIG. 7, the control unit 102 has an internal memory to store a control program such as an OS (Operating System), a program that defines various procedures, and required data, and performs information processing to execute various processes by these programs or the like. The control unit 102 functionally conceptually includes a maximum value-calculating unit 102a, a polymorphic identification character-enumerating unit 102b, a character string-creating unit 102c, a haplotype character string-storing unit 102d, a haplotype-estimating unit 102e, a partitioning unit 102g, a ligating unit 102h, a count number table-creating unit 102j, and a copy number-setting unit 102k. The following explanation will be described in association with the symbols used above to facilitate understanding.

The maximum value-calculating unit 102a calculates a sum of the count numbers (c) for each of the marker sites (M) based on the count number data of the individual stored in the count number table 106a to obtain a maximum value of the sum of the count numbers (c).

The polymorphic identification character-enumerating unit 102b enumerates polymorphic identification characters ($F_1$, $F_2$, $F_3$, or the like) associated with the type of the polymorphic nucleotides up to the number as many as the count numbers (c) of the polymorphic nucleotides. The polymorphic identification character-enumerating unit 102b may enumerate the polymorphic identification character (for example, $F_0$) indicating a nucleotide deletion as a type of the polymorphic nucleotide up to the number as many as the number obtained by subtracting the sum from the maximum value calculated by the maximum value-calculating unit 102a.

The character string-creating unit 102c permutates the polymorphic identification characters enumerated by the polymorphic identification character-enumerating unit 102b so as to create any character string that has copy units (u) of which the number equals the maximum value. The character string-creating unit 102c may confirm that the number of the polymorphic identification characters in the created character string and the count number (c) of the polymorphic nucleotide for each type in the count number table 106a conform to each other, and eliminate the character string when they are not conform to each other.

The haplotype character string-storing unit 102d divides the character string created by the character string-creating unit 102c into two by the copy unit to store the divided strings in the haplotype character string file 106b as a combination of the haplotype character strings.

The haplotype-estimating unit 102e calculates the number of identical haplotype character strings in the group by referencing the haplotype character string file 106b, obtains a frequency of the haplotype character string in the group, and estimates the combination of the haplotype character strings (representing haplotypes) of each individual of which frequency satisfying a predetermined condition. The haplotype-estimating unit 102e may calculate the frequency of the haplotype character string based on the Hardy-Weinberg Principle, and use a Hardy-Weinberg equilibrium in the group as the predetermined condition.

As shown in FIG. 7, the haplotype-estimating unit 102e includes a haplotype frequency-calculating unit 102f. The haplotype frequency-calculating unit 102f repeats an M step of calculating the frequency of the haplotype character string in the group by weighting with the frequency of the combination having the haplotype character string as one of them, and an E step of obtaining the frequency of the combination by a product of the frequencies of the two haplotype character strings composing the combination to calculate the weight based on the frequencies of the combination, until a value of the frequency converges, using an expectation-maximization (EM) algorithm. The haplotype frequency-calculating unit 102f may obtain log likelihood difference between the frequency of the haplotype character string calculated at the M step and the frequency of the haplotype character string calculated at the previous M step, and judge that a value of the frequency is converged when the log likelihood difference is equal to or smaller than a predetermined threshold. As a result, a convergence condition of the EM algorithm can be appropriately set, so that calculation time can be reduced while assuring accuracy.

The haplotype frequency-calculating unit 102f may calculate the frequency $P(h_i)$ of the haplotype character string based on a following mathematical expression 1 at the M step, obtain the frequency $P(d_{jk})$ of the combination of the haplotype character strings based on a following mathematical expression 2, and calculate the weight $w_{jk}$ by dividing the frequency of the combination of the haplotype character strings by a sum total of the frequency of the combination in the group at the E step.

$$P(h_i) = \frac{\sum_j \sum_k N(c_j) \cdot \delta(h_j, d_{jk}) \cdot w_{jk}}{2n} \quad \text{(Expression 1)}$$

In the mathematical expression above, $P(h_i)$ represents the frequency of the haplotype character string, h represents the haplotype character string, and i represents an index of the haplotype character string. Also, n represents the number of the individuals composing the group, j represents an index of a pattern of the count number in the count number table, k is an index of the combination of the haplotype character string, and N ($c_j$) represents the number of the individuals having a pattern j of the count number. Also, $\delta(h_i, d_{jk})$ is a function to return 1 when a combination $d_{jk}$ of the haplotype character strings has the haplotype character string $h_i$ on one side, return 2 when this has the haplotype character string on both sides, and return 0 when this does not have the haplotype character string $h_i$, and $d$ represents the combination of the haplotype character strings. Also, $w_{jk}$ is the weight by the frequency of the combination of the haplotype character strings.

$$P(d_{jk}) = P(h_1 \oplus h_m) = \begin{cases} P(h_1)P(h_m) & \text{if } 1 = m \\ 2P(h_1)P(h_m) & \text{if } 1 \neq m \end{cases} \quad \text{(Expression 2)}$$

In the mathematical expression above, $P(d_{jk})$ represents the frequency of the combination of the haplotype character strings. Also, $h_i$ and $h_m$ represent two haplotype character strings composing the combination, and $P(h_i)$ and $P(h_m)$ represent the frequencies of the two haplotype character strings, respectively.

Returning to the explanation of FIG. 7, the partitioning unit 102g partitions the copy unit (u) into multiple partitions by a unit of the marker sites (M), and, for the nucleotide polymorphism of the marker sites included in the partition, controls the maximum value-calculating unit 102a, the polymorphic identification character-enumerating unit 102b, the character string-creating unit 102c, the haplotype character string-storing unit 102d, and the haplotype-estimating unit 102e to execute the process for each of the partitions. In other words, the partitioning unit 102g executes Partition step based on the Partition-Ligation method.

The ligating unit 102h reproduces the haplotype character string composed of the partitions by ligating each of the partitions on the copy unit (u) with each other between the haplotype character strings having same repeat pattern of the copy unit (u), for the haplotype character string estimated by the haplotype-estimating unit 102e for each of the partitions. In other words, the ligating unit 102h executes Ligation step based on the Partition-Ligation method. This is an internal configuration of the haplotype estimating apparatus 100.

The count number table-creating unit 102j counts polymorphic nucleotides associated with the marker sites by using the genotype data for each individual stored in the genotype data file 106c and stores the count numbers for each type of the polymorphic nucleotides in the count number table 106a. The count number table-creating unit 102j may create the count number table 106a in which the copy number summation in each individual stored in the copy number summation file 106d is regarded as the count number of any one of the polymorphic nucleotides.

The copy number-setting unit 102k calculates the number of the polymorphic identification characters associated with the one polymorphic nucleotide in the haplotype character string in the combination of the haplotypes estimated by the haplotype-estimating unit 102e, and sets the calculated number as the copy number in the haplotype.

The haplotype estimating apparatus 100 may be communicably connected to a network 300 through a communication device such as a router or a wired or wireless communication line such as a leased line. In this case, the system includes the haplotype estimating apparatus 100, and an external system 200 which provides an external program such as a haplotype estimating program and an external database related to count number data through the network 300. In FIG. 7, the network 300 has a function of connecting the haplotype estimating apparatus 100, and the external system 200 with each other. For example, the Internet is used as the network 300.

The external system 200 is mutually connected to the haplotype estimating apparatus 100 through the network 300 and has a function of providing an external database related to count number data, or a web site which executes an external program such as a haplotype estimating program to a user. In this case, the external system 200 may be designed to serve as a WEB server or an ASP server. The hardware configuration of the external system 200 may be constituted by an information processing device such as a commercially available workstation or personal computer and a peripheral device thereof. The functions of the external system 200 are realized by a CPU, a disk device, a memory device, an input device, an output device, a communication control device, and the like in the hardware configuration of the external system 200 and programs which control these devices. This is the explanation of the configuration of the haplotype estimating apparatus 100.

Processing of the Haplotype Estimating Apparatus 100

An example of processing of the haplotype estimating apparatus 100 according to the embodiment constructed as described above will be explained below in detail with reference to FIGS. 8 to 12.

Haplotype Estimating Processing

Figure 8:
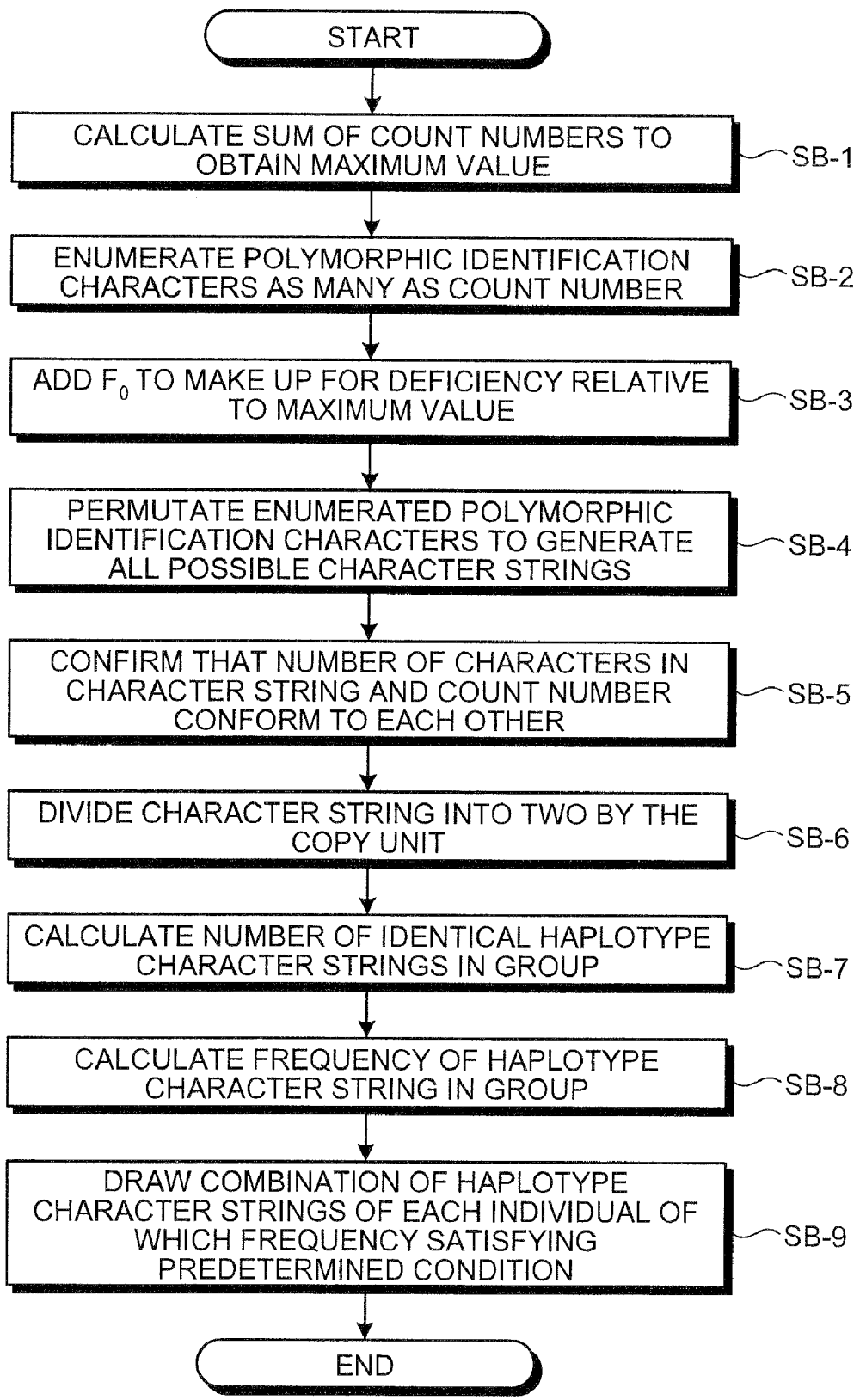
FIG. 8 is a diagram showing an example of the haplotype estimating process of the haplotype estimating apparatus 100.

An example of haplotype estimating processing according to the haplotype estimating apparatus 100 will be explained below. FIG. 8 is a diagram showing an example of the haplotype estimating processing of the haplotype estimating apparatus 100.

As shown FIG. 8, the maximum value-calculating unit 102a calculates a sum of the count numbers (c) for each of the marker sites (M) based on the count number data of the individual stored in the count number table 106a to obtain a maximum value of the sum of the count numbers (c) (SB-1). Before this process, the count number table-creating unit 102j counts polymorphic nucleotides associated with the marker sites (M) by using the genotype data for each individual stored in the genotype data file 106c and stores the count numbers (c) for each type of the polymorphic nucleotides in the count number table 106a.

The polymorphic identification character-enumerating unit 102b enumerates polymorphic identification characters ($F_1$, $F_2$, $F_3$, or the like) associated with the type of the polymorphic nucleotides up to the number as many as the count numbers (c) of the polymorphic nucleotides (SB-2).

The polymorphic identification character-enumerating unit 102b enumerates the polymorphic identification character ($F_0$) indicating a nucleotide deletion up to the number as many as the number obtained by subtracting the sum from the maximum value calculated by the maximum value-calculating unit 102a (SB-3). Here, the number of the enumerated polymorphic identification characters is equal to the number obtained by multiplying the maximum value by the number of the copy units.

The character string-creating unit 102c permutates the polymorphic identification characters enumerated by the polymorphic identification character-enumerating unit 102b so as to create any character string that has copy units of which the number equals the maximum value (SB-4).

The character string-creating unit 102c may confirm that the number of the polymorphic identification characters in the created character string and the count number (c) of the polymorphic nucleotide for each type in the count number table 106a conform to each other, and eliminate the character string when they are not conform to each other (SB-5). Here, since the data of the number of the polymorphism of the nucleotide deletion is not stored in the count number table 106a, as a matter of course, it is not required to confirm conformance with the number of the polymorphic identification character ($F_0$) representing the nucleotide deletion.

The haplotype character string-storing unit 102d divides the character string created by the character string-creating unit 102c into two by the copy unit to store the divided strings in the haplotype character string file 106b as a combination of the haplotype character strings (SB-6). For example, the four combinations may be generated in the character string having the three copy units, the five combinations may be generated in the character string having the four copy units, and (N+1) combinations may be generated in the character string having the N copy units.

The haplotype-estimating unit 102e calculates the number of identical haplotype character strings in the group by referencing the haplotype character string file 106b that stores the combinations of the haplotype character strings stored by the character string-creating unit 102c (SB-7).

The haplotype-estimating unit 102e calculates a frequency of the haplotype character string in the group (SB-8). The haplotype-estimating unit 102e may calculate the frequency of the haplotype character string based on the Hardy-Weinberg Principle.

The haplotype-estimating unit 102e draws the combination of the haplotype character strings of each individual of which frequency satisfying a predetermined condition to estimate the combination of the haplotypes (SB-9). The haplotype-estimating unit 102e may use a Hardy-Weinberg equilibrium in the group as the predetermined condition.

Maximum Value Calculating Processing to Haplotype Character String Storing Processing An example of a maximum value calculating processing to a haplotype character string storing processing for obtaining possible combination of the haplotypes is explained below in detail with reference to FIG. 9.

As an example of a method of obtaining the possible combination of the haplotypes without deficiency and excess, that is to say, a method of finding the diplotype (the combination of the haplotypes) consistent with the count number data, there is a method of first finding the set of the copy units (u) consistent with the count number data (corresponding to a polymorphic identification character-enumerating unit by the polymorphic identification character-enumerating unit 102b), and then composing the diplotype (the combination of the haplotypes) (corresponding to the haplotype character string-storing unit by the haplotype character string-storing unit 102d). The set of the copy units consistent with the count number data means that when summing up the count numbers (c) of each polymorphic nucleotide in each marker site (M) of the copy unit (u) across all of the copy units (u) belonging to the set of the characters (character string), a total count number (c) of each polymorphic nucleotide in each marker site (M) conforms to the count number of each nucleotide in each marker site in the count number data stored in the count number table 106a. FIG. 9 is a flowchart of an example of a process to create the diplotype consistent with the count number pattern in all the patterns of the count number data.

Figure 9:
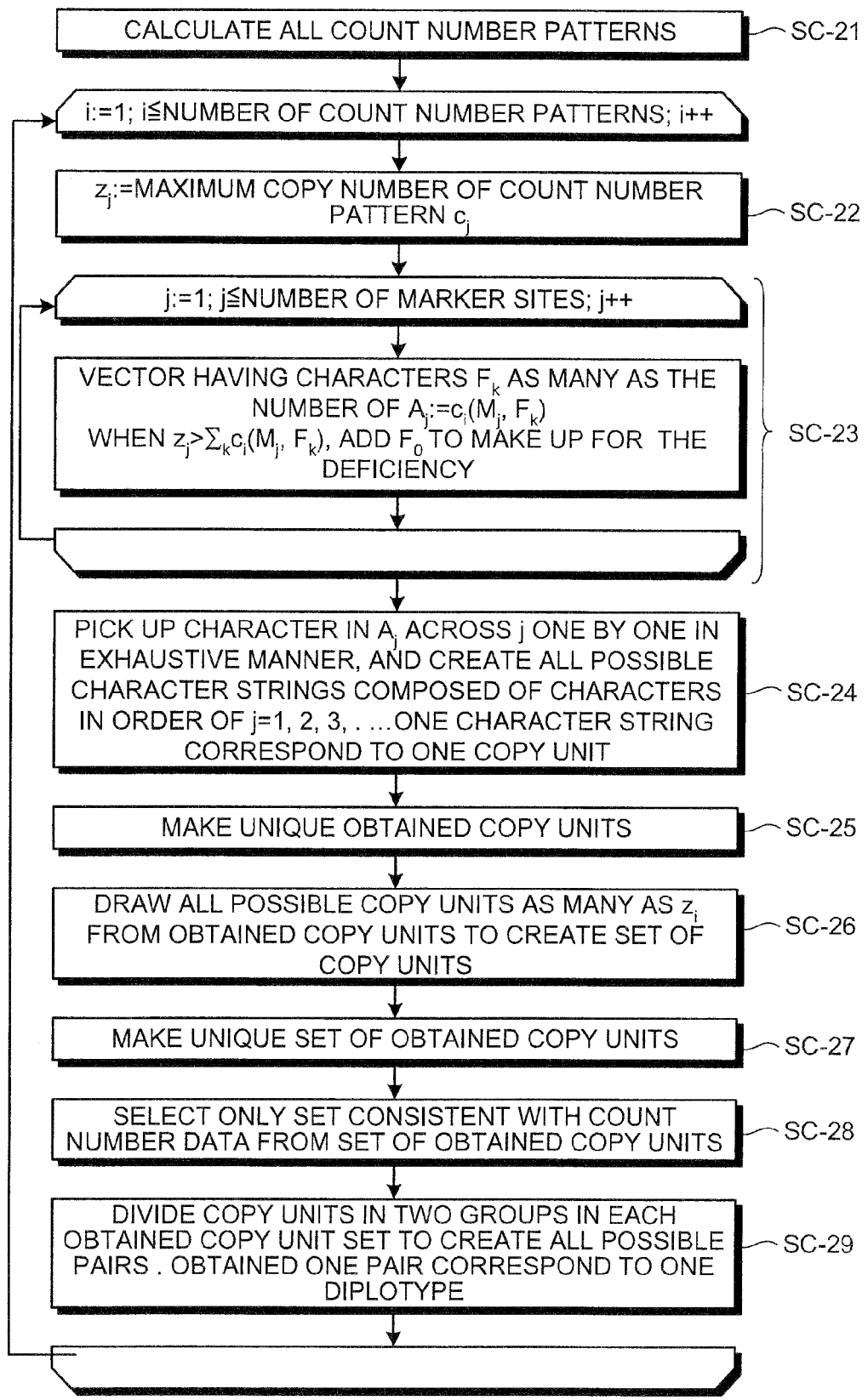
FIG. 9 is a flowchart of an example of a process to create the diplotype consistent with the count number pattern in all the patterns of the count number data.

As shown in FIG. 9, the character string-creating unit 102c first calculates a unique count number pattern ($c_i$) from the count number data stored in the count number table 106a (SC-21).

The haplotype estimating apparatus 100 enters an iteration of the count number pattern (i) (i iteration). The iteration first initializes i to 1, increments i by one for each iteration, and repeats this as long as "i<=the number of count number patterns". In the i iteration, the maximum value-calculating unit 102a finds a count total number (sum) that has the maximum value regarding j, where count total number: (sum) $s_j = \Sigma_k c_i(M_j, F_k)$ and sets this as a maximum copy number $z_i$ (SC-22).

The haplotype estimating apparatus 100 enters the iteration regarding the marker site (M) (j iteration) (SC-23). The j iteration first initializes j to 1, increments by one for each iteration, and repeats this as long as "j<=the number of marker sites". In the j iteration, the polymorphic identification character-enumerating unit 102b enumerates the polymorphic identification characters $F_k$ as many as the count number $c_i(M_j, F_k)$ across all k for each marker site $M_i$. When the count total number $s_i$ is less than the maximum copy number $z_1$, the polymorphic identification character-enumerating unit 102b makes up for the deficiency with the polymorphic identification character $F_0$ representing the nucleotide deletion. The character string-creating unit 102c creates a vector $A_j$ representing a group of the polymorphic identification characters included in a certain marker site (M) from a group of the polymorphic identification characters $F_k$ enumerated by the polymorphic identification character-enumerating unit 102b ($A_1 = (F_1, F_1, F_2)$ in $M_1$ shown in FIG. 6, for example). In this manner, the haplotype estimating apparatus 100 terminates the j iteration.

The character string-creating unit 102c picks up the polymorphic identification character group in $A_j$ one by one across each j, and creates all possible character strings in the order of j=1, 2, 3, (SC-24). For example, when vector $A_1=(a_1, a_2)$, $A_2=(b_1, b_2)$, $A_3=(C_1, c_2)$, all possible character strings are created as $a_1b_1c_1$, $a_1b_1c_2$, $a_1b_2c_1$, $a_1b_2c_2$, $a_2b_1c_1$, $a_2b_1c_2$, $a_2b_2c_1$, and $a_2b_2c_2$. One character string created by the character string-creating unit 102c corresponds to one copy unit.

The character string-creating unit 102c makes the obtained copy units unique. To makes it unique is to eliminate same excess ones (SC-25).

The character string-creating unit 102c draws the copy units as many as the maximum copy number $z_i$ in every combination from the obtained copy units to create the sets of the copy units in every combination (SC-26). As a result, any character string in which the copy unit is repeated up to the number of times as many as the maximum value (maximum copy number) may be obtained.

The character string-creating unit 102c makes the obtained character strings (the set of the copy units) unique (SC-27).

The character string-creating unit 102c selects only the set consistent with the count number data from the obtained character strings using a following mathematical expression (SC-28). That is to say, the character string-creating unit 102c confirms that the number of the polymorphic identification characters in the created character string and the count number for each type of the polymorphic nucleotide in the count number table 106a conform to each other using the following mathematical expression (or something mathematically equal to the same), and eliminates the character string when they are not conform to each other.

$$c_i(M_j, F_k) = \sum_1 \delta(F_k, u_1(M_j))(k \neq 0),$$

wherein $$\delta(F_k, u_1(M_j)) = \begin{cases} 1 & \text{if } u_1(M_j) = F_k \\ 0 & \text{if } u_1(M_j) \neq F_k \end{cases}$$

In the mathematical expression above, $c_i$ represents a count number pattern. Herein, i is an index indicating the pattern and is not the index indicating the individual (when different individuals have the same count number pattern, the pattern is represented as identical $c_i$). Also, $c_i(M_j, F_k)$ represents the count number of the polymorphic nucleotide $F_k$ in the marker site $M_j$ (for example, in the pattern of the individual 1 in FIG. 4 explained above, $c_1(M_1, F_1)=2$, $c_1(M_2, F_1)=1$). $u_1$ represents the copy unit and $u_1(M_j)$ represents the polymorphic nucleotide (including $F_0$, which means the nucleotide deletion) in the marker site $M_j$ of the copy unit (for example, in FIG. 3 explained above, $u_1(M_1)=F_1$, $u_2(M_2)=F_3$, $u_3(M_3)=F_0$, and $u_0(M_1)=F_0$).

The haplotype character string-storing unit 102d divides each obtained character string into two by the copy unit to create the two haplotype character strings as one pair for all the character strings, and stores them in the haplotype character string file 106b (SC-29). For example, when dividing into two by "/", four groups, which are [/$F_1F_1F_2$, $F_1F_1F_0$, $F_1F_2F_2$], [$F_1F_1F_2/F_1F_1F_0$, $F_1F_2F_2$], [$F_1F_1F_2$, $F_1F_1F_0/F_1F_2F_2$], and [$F_1F_1F_2$, $F_1F_2F_2$, $F_1F_0F_0/$], are created for [$F_1F_1F_2$, $F_1F_1F_0$, $F_1F_2F_2$]. The one pair of the two haplotypes character strings herein obtained corresponds to one diplotype. The haplotype character string-storing unit 102d may add a pair of the character string in which all the polymorphic identification characters are $F_0$ and all of the copy units as a special combination (such as [$F_0F_0F_0/F_1F_1F_2$, $F_1F_1F_0$, $F_1F_2F_2$])

The haplotype estimating apparatus 100 performs the above-explained process for each count number pattern, terminates the i iteration, and finally generates all of the diplotypes consistent with the count number data. This is the detailed explanation of one example of a maximum value calculating processing to a haplotype character string storing processing for obtaining possible combination of the haplotypes. The haplotype-estimating unit 102e calculates a frequency of the haplotype character string in the group by using the combinations of the haplotype character strings obtained by the maximum value calculating processing to the haplotype character string storing processing.

Processing Using EM Algorithm

An example of processing of EM algorithm by processing of the haplotype-estimating unit 102e will be explained below in detail. The haplotype-estimating unit 102e effectively calculates a frequency of the haplotype character string in the group by using EM algorithm by processing of the haplotype frequency-calculating unit 102f.

The EM algorithm is a method of allocating weight of presence to the obtained diplotype (the combination of the haplotype character strings in this embodiment), counting the number of the haplotypes included in the diplotype in consideration of the weight, calculating the frequency of the haplotype (M step), then updating the weight of the presence of the diplotype using the Hardy-Weinberg Principle from the haplotype frequency (E step), and further, repeating the process as the M step, next the E step, further the M step, . . . , using the updated weight, thereby updating the frequency. For example, the M step based on the following mathematical expression 1 and the E step based on the following mathematical expression 2 are mutually repeated to update the frequency of the haplotype.

<M step> (Expression 1)

$$P(h_i) = \frac{\sum_j \sum_k N(c_j) \cdot \delta(h_i, d_{jk}) \cdot w_{jk}}{2n}$$

wherein $$\delta(h_i, d_{jk}) = \begin{cases} 2 & \text{if } d_{jk} \text{ includes two } h_i \\ 1 & \text{if } d_{jk} \text{ includes one } h_i \\ 0 & \text{if } d_{jk} \text{ includes no } h_i \end{cases}$$

In the mathematical expression above, $P(h_i)$ represents the frequency of the haplotype character string, h represents the haplotype character string, and i represents an index of the haplotype character string. Also, n represents the number of the individuals composing the group, j represents an index of a pattern of the count number, k is an index of the combination of the haplotype character string, and $N(c_j)$ represents the number of the individuals having a pattern j of the count number. Also, $\delta(h_i, d_{jk})$ is a function to return 1 when a combination $d_{jk}$ has the haplotype character string $h_i$ on one side, return 2 when this has the haplotype character string $h_i$ on both sides, and return 0 when this does not have the haplotype character string $h_i$, and d represents the combination of the haplotype character strings. Also, $w_{jk}$ is the weight by the frequency of the combination of the haplotype character strings.

<E step> (Expression 2-1)

$$w_{jk} = \frac{P(d_{jk})}{\sum_k P(d_{jk})}$$

In the mathematical expression above, $P(d_{jk})$ is calculated based on the following mathematical expression 2-2 that represents Hardy-Weinberg Principle.

<Hardy-Weinberg Principle> (Expression 2-2)

$$P(d_{jk}) = P(h_1 \oplus h_m) = \begin{cases} P(h_1)P(h_m) & \text{if } 1 = m \\ 2P(h_1)P(h_m) & \text{if } 1 \neq m \end{cases}$$

"$d_{jk}=h_1 \oplus h_m$" represents that the combination $d_{jk}$ of the haplotype character strings is composed of the haplotype character string $h_1$ and the haplotype character string $h_m$.

The above-explained mathematical expression. 2-2 represents the Hardy-Weinberg Principle, which is a natural law in genetics thereby the two haplotypes composing the diplotype and the probability (or frequency) thereof are known, the probability (or frequency) of the diplotype can be calculated. In the above-explained EM algorithm, it is interpreted that the haplotype with very low frequency is not present. The haplotype-estimating unit 102e estimates the combination of the haplotypes and the frequency thereof using the above-explained EM algorithm as an example, by the process of the haplotype frequency-calculating unit 102f. The haplotype frequency-calculating unit 102f may obtain the log likelihood difference between the frequency of the haplotype character string calculated at the M step and the frequency of the haplotype character string calculated at the previous M step based on a following mathematical expression, and judge that the value of the frequency converges when the log likelihood difference is equal to or smaller than the predetermined threshold.

$$\log \prod_j \left\{ \sum_k P(d_{jk}) \right\}^{N(c_j)}$$

Processing Using PL Strategy

An example of processing using PL strategy will be explained below with reference to FIGS. 10 to 12.

Although the combination of the haplotype character strings and the frequency thereof can be estimated with a logical reason from the count number data stored in the count number table 106a by a process of the maximum value-calculating unit 102a to the haplotype-estimating unit 102e, when the number of the marker sites (M) increases, the number of possible haplotypes drastically increases, so that calculation time becomes enormous. In such a case, a Partition-Ligation (PL) strategy is used as a method of reducing the calculation time. FIG. 10 is an illustration of an example of ligation process in the PL strategy in the haplotype estimating method, which does not take the copy number polymorphism into consideration.

As shown in FIG. 10, the PL strategy partitions the loci (L) into less partitions (partitioned loci in FIG. 10) (partition step), and estimates the combination of the haplotypes and the frequency thereof for each partition in the partition, and eliminates the haplotype of which frequency is low (the haplotype is sometimes recovered by a criterion other than the frequency). Regarding remaining haplotypes, the haplotypes are ligated between the partitions (generally, adjacent partitions) (ligation step, ligated loci in FIG. 10) and the frequency of the ligated haplotypes is estimated using the genotype data of the ligated partitions for the ligated haplotypes. Herein, "to ligate the haplotypes" corresponds to ligate the character strings to create a longer character string when the haplotype is considered as the character string ("haplotype character string" in this embodiment). The PL strategy can not be directly applied to the genotype data including the copy number polymorphism and the nucleotide polymorphism in this embodiment. That is to say, since each marker site is separated by the copy unit in this embodiment, the adjacent loci can not be ligated at the ligation step. FIG. 11 is an illustration of an example of the ligation process in the PL strategy of the haplotype estimating method in consideration of the copy number polymorphism according to this embodiment. Herein, $h_0$ represents a deletion haplotype in which the number of copy unit is 0.

As shown in FIG. 11, in the present embodiment, the partitioning unit 102g partitions the copy unit (u) into multiple partitions (Partitioned markers) by a unit of the marker sites (M), and, for the nucleotide polymorphism of the marker sites included in the partition, controls the maximum value-calculating unit 102a~the haplotype frequency-calculating unit 102f to execute the process for each of the partitions (partition step). Then, the ligating unit 102h reproduces the haplotype character string composed of the partitions by ligating each of the partitions on the copy unit (u) with each other between the haplotype character strings having same repeat pattern of the copy unit (in the case of FIG. 11, between h1 and h4, or between h2 and h5), for the haplotype character string calculated in each of the partitions (ligation step). FIG. 12 is an illustration of a logical ligating method at the ligation step.

Figure 12:
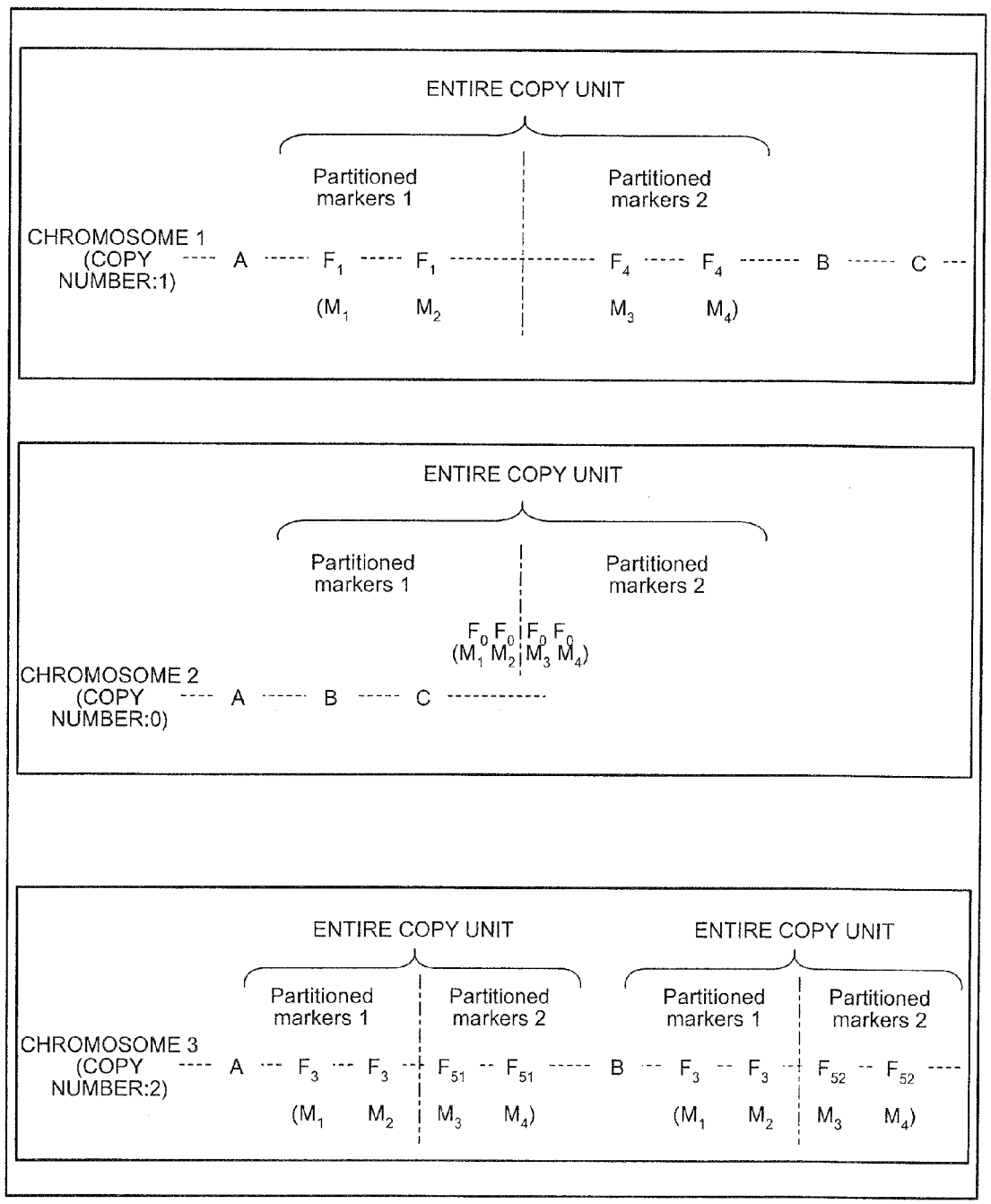
FIG. 12 is an illustration of a logical ligating method at the ligation step.

That is to say, as shown in FIG. 12, the ligating unit 102h ligates the haplotype character strings having the same number of copy units (u), without the copy unit left over, when performing the ligation step of the haplotype character strings between different partitions, and creates a new haplotype. To "ligate the copy units" corresponds to create a longer character string by ligating the character strings when the copy unit is considered as the character string. The ligating unit 102h performs the process to ligate the copy units of the haplotype, without the copy unit left over, in every combination of the copy units (for example, refer to the chromosome 3 in FIG. 12). The logical reason thereof is that the partition in a unit of multiple marker sites (M) at the partition step does not correspond to partition of the haplotype as in the Pt strategy, which does not take the above-explained copy number polymorphism into consideration, but this corresponds to partition the copy units in this embodiment.

Second Embodiment

A second embodiment using copy number summation for each individual will be explained blow with reference to FIGS. 13 and 14.

In the second embodiment, the haplotype is estimated not only from the count number data of the polymorphic nucleotide identified by the label such as the fluorochrome probe as in the first embodiment but also from the summation (summation across two homologous chromosomes) data of the copy numbers of the copy number polymorphism obtained by any experimental technique. That is to say, the haplotype estimating apparatus 100 estimates the copy number present in the haplotype and the frequency of the haplotype using the copy number summation data of the copy number polymorphism in each individual stored in the copy number summation file 106d. It is not necessary that the polymorphic nucleotide is present on the copy unit, which is a target of the haplotype estimation, in the second embodiment. FIG. 13 is a flowchart of an example of processing according to the second embodiment.

Figure 13:
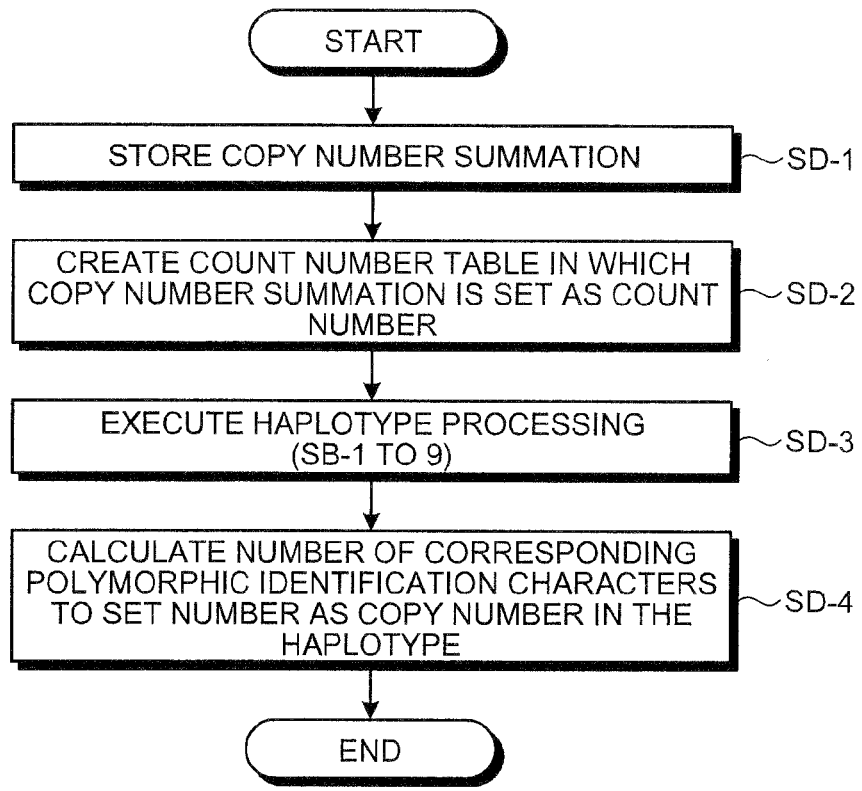
FIG. 13 is a flowchart of an example of processing according to the second embodiment.

As shown in FIG. 13, the copy number summation file 106d stores a copy number summation of the copy number polymorphism in each individual (SD-1). The "copy number summation" means the summation of the numbers of the copy units across the two homologous chromosomes.

Next, the count number table-creating unit 102j creates the count number table 106a in which the copy number summation in each individual stored in the copy number summation file 106d is regarded as the count number of any one of the polymorphic nucleotides (SD-2). FIG. 14 is an illustration of an example of correspondence relationship between the copy number summation data and the created count number table in each individual.

Figure 14:
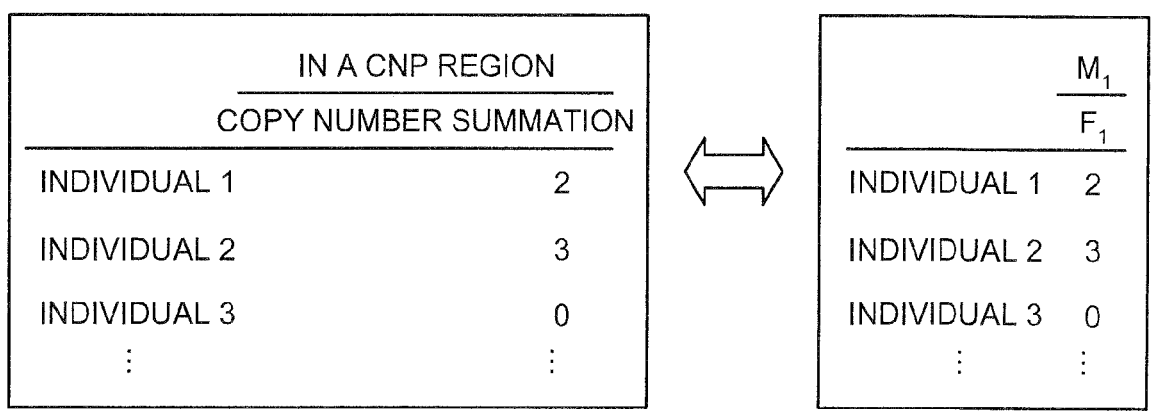
FIG. 14 is an illustration of an example of correspondence relationship between the copy number summation data and the created count number table in each individual.

The count number table-creating unit 102j provisionally treats the copy number summation 2, 3, 0 . . . as the count number of the polymorphic nucleotide of one type ($F_1$) in the marker site ($M_1$) as shown in FIG. 14 right, based on the copy number summation data of each individual 1, 2, 3 . . . in a certain copy number polymorphism (CNP) region stored in the copy number summation file 106d as shown in FIG. 14, left, to create the count number table 106a. That is to say, in the example shown in FIG. 14, since the copy number summation of the individual 1 is "2" and the copy number summation of the individual 2 is "3", the count number table-creating unit 102j creates the count number table 106a in which a count number of the provisional polymorphic nucleotide $F_1$ in the marker site $M_1$ is set to "2" for the individual 1, and the count number of the provisional polymorphic nucleotide $F_1$ in the marker site $M_1$ is set to "3" for the individual 2.

The haplotype estimating apparatus 100 executes the haplotype estimation process (SB-1 to 9) explained with reference to FIG. 8 in the first embodiment, based on the created count number table 106a (SD-3). For example, in the example shown in FIG. 14, the haplotype estimating apparatus 100 creates [$F_0/F_1$, $F_1$] and [$F_1/F_1$] as the combinations of the haplotype character strings for the individual 1, and creates [$F_0/F_1$, $F_1$, $F_1$] and [$F_1/F_1$, $F_1$] as the combinations of the haplotype character strings for the individual 2, to perform the haplotype estimation process. Herein, $F_1$ represents the polymorphic identification character associated with the above-explained arbitrary one polymorphic nucleotide, and $F_0$ is the polymorphic identification character representing that the copy number is 0.

The copy number-setting unit 102$k$ calculates the number of the polymorphic identification character ($F_1$) associated with the one polymorphic nucleotide in the haplotype character string in the combination of the haplotypes estimated by the haplotype-estimating unit 102$e$, and sets the calculated number as the copy number in the haplotype (SD-4). For example, the copy number-setting unit 102$k$ counts the polymorphic nucleotides $F_1$ in the haplotype character strings [$F_0$], [$F_1$], [$F_1$, $F_1$], [$F_1$, $F_1$, $F_1$] in the combinations of the haplotypes estimated by the process of the haplotype-estimating unit 102$e$, and sets them as the copy numbers [0], [1], [2], [3], respectively. Therefore, the copy number (the number of copy units) present in an object haplotype and the frequency of the haplotype can be obtained. For example, the haplotypes of the copy number polymorphism of which copy numbers are 0, 1, 2 and 3 and the frequencies thereof can be obtained, for example. This is the end of the explanation of the second embodiment.

EXAMPLE

An implementation example of the above-explained embodiment using a programming language Perl is hereinafter explained with reference to FIGS. 15 to 30.

Example of EM Algorithm

Figure 15:
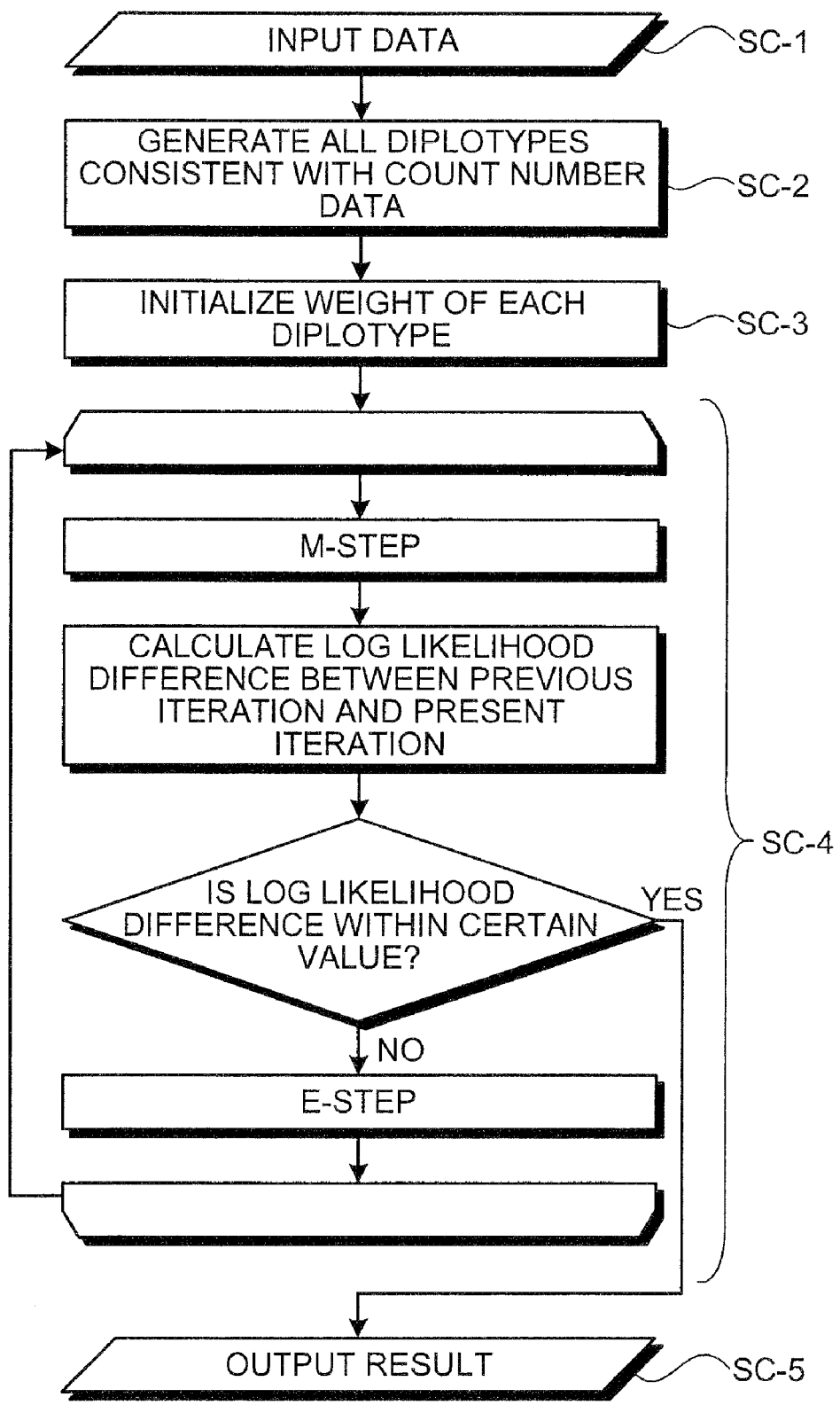
FIG. 15 is a flowchart of an example of the haplotype estimation process by the EM algorithm.

An example of the haplotype estimation process by the EM algorithm in this example is explained. FIG. 15 is a flowchart of an example of the haplotype estimation process by the EM algorithm. In the following explanation, the haplotype character string and the combination of the haplotype character strings in this embodiment are sometimes simply referred to as the "haplotype" and the "diplotype", respectively.

As shown in FIG. 15, first, the maximum value-calculating unit 102$a$ refers to the count number table 106$a$ to read the count number data (SC-1). At the same time, a numeric value of the convergence test by the process of the haplotype frequency-calculating unit 102$f$ may be read.

The haplotype estimating apparatus 100 performs the processes (SC-21 to SC-29) explained in the Maximum Value Calculation Process~Haplotype Character String Storing Process section with reference to FIG. 9 (SC-2)

In a subsequent step, the haplotype-estimating unit 102$e$ calculates the frequency of the haplotype character string based on the combination of the haplotype character strings stored in the haplotype character string file 106$b$ and the count number data stored in the count number table 106$a$ using the EM algorithm by the process of the haplotype frequency-calculating unit 102$f$.

That is to say, first, the haplotype frequency-calculating unit 102$f$ initializes the weight of the presence of each combination of the haplotypes for each count number pattern ($c_j$) (SC-3). In this example, the initial value of the weight is equally allocated. That is to say, the initial value of the weight is $w_{jk}=1/n_{jk}$. Herein, w, j, k are the same as those of the above explanation (in the configuration of the haplotype estimating apparatus) (w is weight, j is count number pattern, k is index of diplotype (combination of haplotype character strings) in the count number pattern), and $n_{jk}$ is total number of diplotypes in count number pattern).

Next, shifting to SC-4, the haplotype-estimating unit 102$e$ performs the M step of the EM algorithm based on the mathematical expression 1. The log likelihood is calculated according to a following mathematical expression to store in the storage unit 106. In the following mathematical expression, the reference symbols are the same as the above explanation. The log likelihood is an index indicating how well the calculated frequency of the diplotype explains the count number data, and this is used to judge the conversion of the EM algorithm in this example. The haplotype-estimating unit 102$e$ calculates difference between the log likelihood stored in the previous SC-4 iteration and the log likelihood calculated in the present SC-4 iteration in the convergence test, and when the difference is within a certain value, judges that the log likelihood is not improved any more to shift the process to SC-5. Otherwise, the haplotype-estimating unit 102$e$ stays in SC-4 and performs the E step of the EM algorithm according to the mathematical expression 2, and the iteration of SC-A is repeated.

$$\log \prod_j \left\{ \sum_k P(d_{jk}) \right\}^{N(c_j)}$$

The haplotype-estimating unit 102$e$ outputs the haplotype and the frequency thereof to a result file when shifting the process to SC-5 according to the above-explained condition.

Demonstration of EM Algorithm by Simulation

Figure 16:
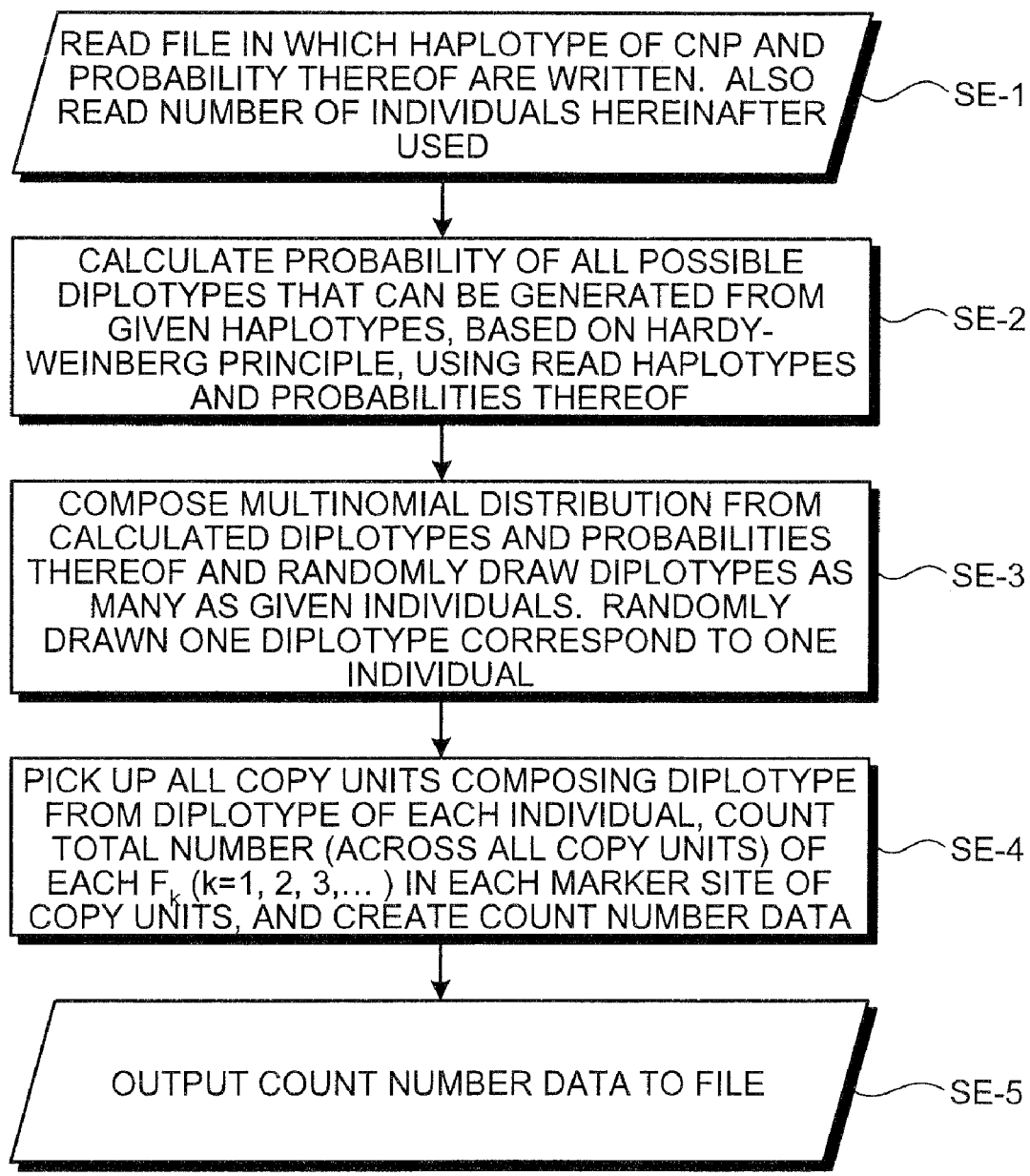
FIG. 16 is a flowchart of a framework of the simulation.

A simulation experiment is performed in order to confirm whether the haplotype of the copy number polymorphism and the frequency thereof can be estimated from the count number data regarding the copy number polymorphism (CNP) in consideration of the nucleotide polymorphism according to this embodiment. That is to say, in the following simulation experiment, the haplotype estimating apparatus 100 performs a process opposite to the haplotype estimation process to derives the count number data from a result (haplotype and probability (frequency)), in order to verify whether the original result can be restored by performing the haplotype estimation process using the count number data. FIG. 16 is a flowchart of a framework of the simulation.

As shown in FIG. 16, the haplotype estimating apparatus 100 reads the file in which the haplotypes of the CNP and the probabilities (frequencies) thereof are written (SE-1). This is the data as shown in FIG. 17, for example (that is to say, the data indicate the result of the haplotype estimation). The haplotype estimating apparatus 100 also reads the number of individuals used in a subsequent process.

The haplotype estimating apparatus 100 creates all possible pairs that are composed of the read haplotypes (a pair composed of two haplotypes), and regards the pair as one diplotype to calculate the probabilities of all the diplotypes from the read probabilities of the haplotypes based on the Hardy-Weinberg Principle (refer to the mathematical expression 2-2) (SE-2).

The haplotype estimating apparatus 100 composes a multinomial distribution of the diplotypes from the diplotypes and the probabilities thereof, and randomly draws the diplotypes as many as the number of given individuals (SE-3). This may be easily performed by a command such as rmultinom (1, size-number of individuals, prob=c (probability of diplotype 1, probability of diplotype 2, probability of diplotype 3, . . . )) using an R language, for example. Each of the diplotypes herein drawn corresponds to (the diplotype of) each individual.

The haplotype estimating apparatus 100 takes out all the copy units (u) composing the diplotype from the diplotype of each individual (SE-4). That is to say, the haplotype estimating apparatus 100 counts the total number (across all the copy units) of each $F_k$ (k=1, 2, 3, . . . ) in each marker site (M) of the copy units (u) to create the count number data. For example, the haplotype estimating apparatus 100 takes out all the copy units [$F_2F_1$, $F_2F_2$, $F_2F_2$] when the diplotype of the individual is [$F_2F_1/F_2F_2$, $F_2F_2$], counts the total numbers of each $F_1$ and $F_2$ in each $M_1$ and $M_2$, and in this case, the total numbers of $F_1$ and $F_2$ in $M_1$ are 0 and 3, respectively, and the total numbers of $F_1$ and $F_2$ in $M_2$ are 1 and 2, respectively.

Finally, the haplotype estimating apparatus 100 outputs the count number data to the file (count number table 106a) (SE-5).

In the framework of the simulation above-explained, the haplotype estimating apparatus 100 read data of the haplotypes and the probabilities thereof as shown in FIG. 17, further read the number of individuals, 500, and created the count number data (FIG. 18).

Subsequently, it was tested whether the haplotype estimating apparatus 100 in this embodiment can estimate (restore) the original haplotypes and the probabilities thereof shown in FIG. 17 only from the output count number data in FIG. 18. In other words, this is an estimation problem of population frequency from incomplete observed data. When applying this embodiment, the threshold of the log likelihood difference used in the convergence test in the EM algorithm was set to be smaller than 0.001.

As a result of applying this embodiment, the haplotype estimating apparatus 100 output a result shown in FIG. 19 regarding the haplotypes and the frequencies thereof. All the frequencies of the haplotypes present in FIG. 19 (restored data) but not present in FIG. 17 (original data) are low. That is to say, it is interpreted that they do not exist. In contrast, all the haplotypes present in FIG. 17 appear in FIG. 19, and estimated frequencies thereof are substantially the same as the correct frequencies. Therefore, it was verified that this embodiment estimates the haplotypes of the CNP and the frequencies thereof with a high accuracy.

Example of PL Strategy

Figure 20:
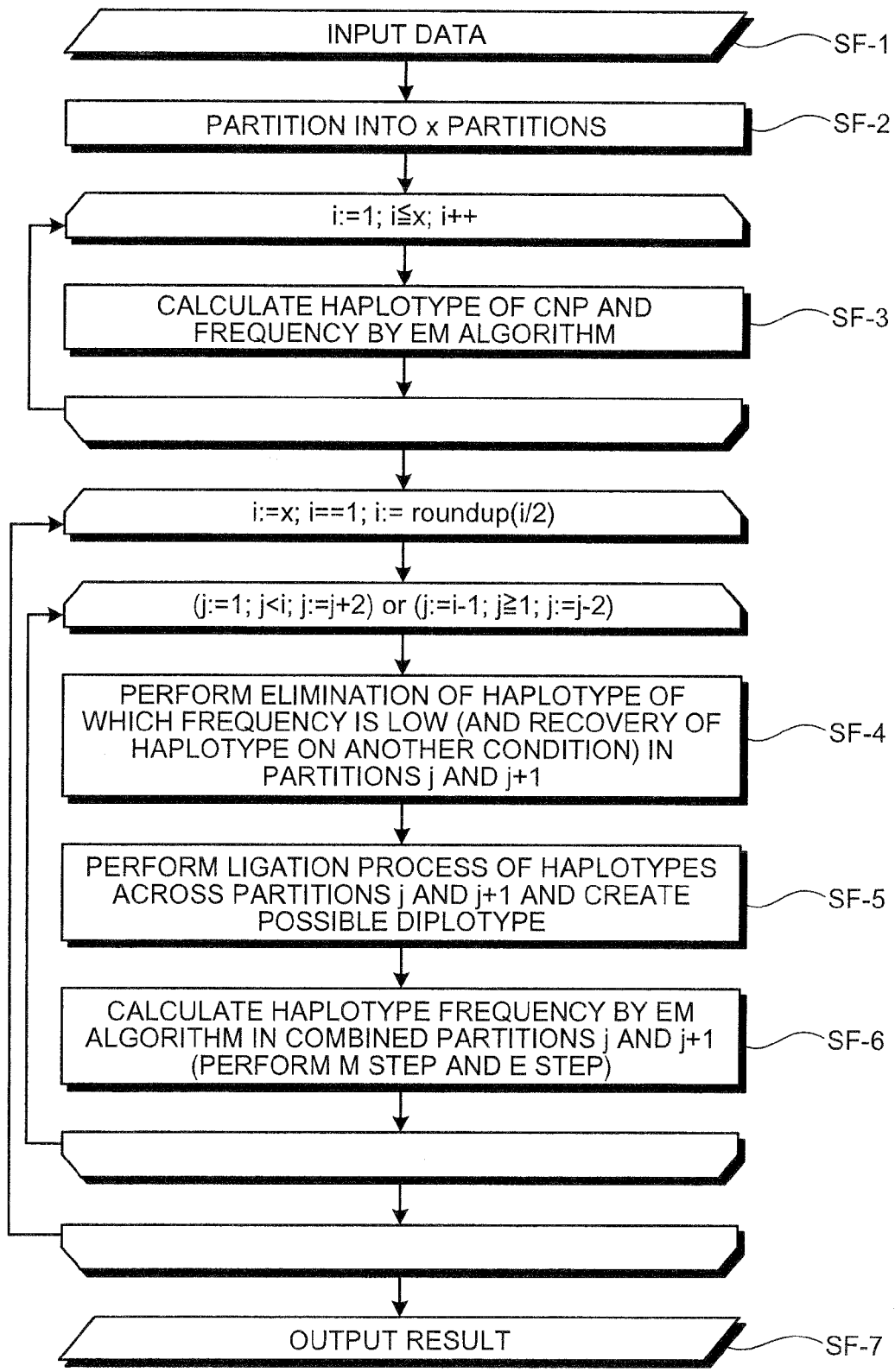
FIG. 20 is a flowchart of a framework of this implement.

An example in which the PL strategy in this embodiment is implemented by the programming language Perl as a hierarchical type of the PL strategy with haplotype buffering is explained hereinafter with reference to FIGS. 20 to 22. FIG. 20 is a flowchart of a framework of this implement.

As shown in FIG. 20, the partitioning unit 102g first reads the count number data (SF-1). The partitioning unit 102g also reads the number of markers of the partition used in the PL strategy, the frequency (a threshold thereof) of the haplotype to be eliminated from the partition, and a haplotype buffer size. The partitioning unit 102g also reads the above-explained parameters required for executing the EM algorithm.

The partitioning unit 102g partitions the read count number data into x partitions from left by the read number of the marker site (M) of the partition (SF-2). An indivisible rightmost partition is composed of the marker sites (M) equal to or smaller than this number.

The partitioning unit 102g enters the iteration (which initializes i to 1 and increments i by one for each one iteration to repeat as long as "i<=x"). In the iteration, the partitioning unit 102g calculates the haplotypes of the CNP and the frequencies thereof by the above-explained EM algorithm by the process of the haplotype frequency-calculating unit 102f for the count number data in each partition (SF-3). For later processes by the PL strategy, an accumulated average frequency of each haplotype in each partition is recorded when executing the process of the haplotype frequency-calculating unit 102f. The accumulated average frequency refers to an average value from start to conversion of the iteration (over the iteration) of the haplotype frequency at each iteration in the EM algorithm.

The haplotype estimating apparatus 100 enters the ligation step by the process of the ligating unit 102h. This consists of SF-4, 5 and 6 and the iteration enclosing them. First, setting of the iteration is explained.

A first iteration (i iteration in FIG. 20) indicates the iteration of a layer in the hierarchical type PL strategy. In the i iteration, in each layer (that is to say, any i), operation in next deeper iteration (j iteration in FIG. 20) is repeated until the number of partitions finally becomes 1. The ligating unit 102h sequentially ligates the partitions in the layer in the next deeper iteration (j iteration). After the ligation, the number of new partitions is roundup (k/2) (herein, k is the number of partitions before the ligation and roundup ( ) means round up). That is to say, the number of partitions after the ligation is half the number of previous partitions when the previous number of partitions is an even number, and is half the number thereof plus one when the previous number is an odd number. In this manner, after the ligation, the number of partitions decreases. That is to say, in the i iteration, the partitions are sequentially ligated in the layer, and after the ligation, the number of partitions is decreased and the process shifts to a next layer. In the next layer also, the partitions are sequentially ligated, and after the ligation, the number of partitions is decreased again and the process shifts to a next layer. The ligating unit 102h repeats the process until the number of partitions finally becomes one.

In the next deeper iteration (j iteration in FIG. 20), all the partitions in the layer are ligated as explained above. The ligation is performed between the adjacent partitions, which are a partition j and a partition j+1. In a first layer, the ligating unit 102h starts j from 1, sequentially increments by two for each iteration, and repeats this as long as j<1. On the other hand, in the next layer, the ligating unit 102h starts j from i−1, the number of all partitions in the layer-1, sequentially decrements by 2, and repeats this as long as j>=1. In this manner, the start of the ligation is set to left and right in turn each time the layer goes to next layer (each time the i iteration is repeated), such as from left in the first layer, from right in the next layer, from left in the subsequent layer, and from right further next layer to repeat the j iteration as explained above. When the number of partitions is the odd number, the last partition is not ligated and is carried over the next layer.

A detail of the process in the iteration is explained hereinafter.

The ligating unit 102h performs elimination of the haplotype of which frequency is low and recovery of the haplotype on another condition in both partitions, which are partitions j and j+1 (SF-4). The recovery of the haplotype on another condition means a process to recover the eliminated haplotype up to the buffer number by the descending order of the accumulated average frequency of the haplotype in the EM algorithm, when the number of remaining haplotypes after the elimination is smaller than a given haplotype buffer size.

The ligating unit 102h executes the ligation process of the haplotypes across a larger partition in which the partition j and the partition j+1 are combined to create the diplotype (combination of the haplotypes) which is composed of the haplotypes and is consistent with the count number data (SF-5). FIG. 21 is a flowchart of an example of a more detailed process of SF-5.

Figure 21:
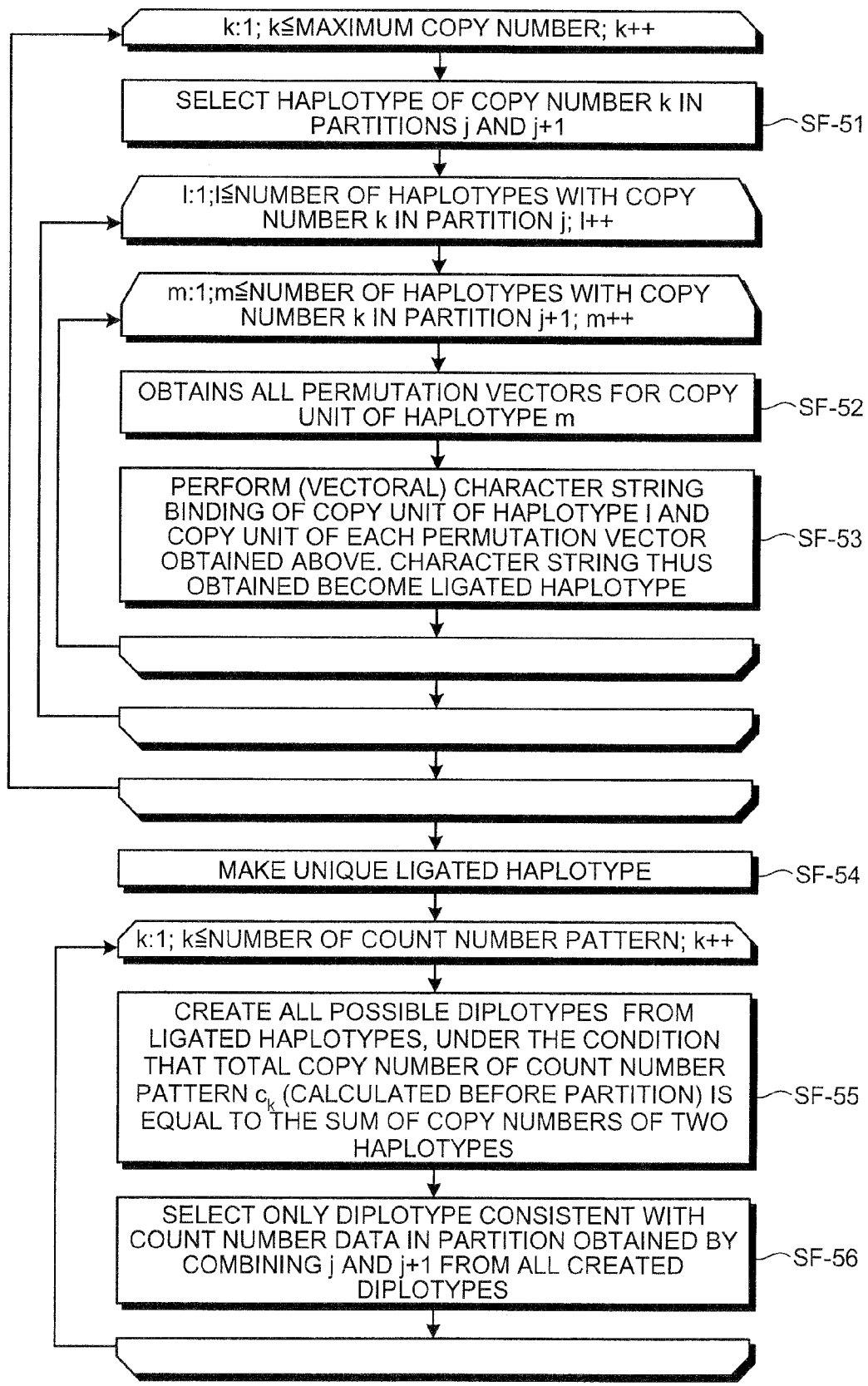
FIG. 21 is a flowchart of an example of a more detailed process of SF-5.

As shown in FIG. 21, the ligating unit 102h first counts the copy numbers of all the haplotypes in the partition j and the partition j+1 to obtain the maximum copy number (SF-51). The ligating unit 102h sets the copy number k to 1, and executes a k iteration until arriving at the maximum copy number. In SF-51 in the iteration, the ligating unit 102h selects the haplotype with the copy number k in the partition j and the partition j+1 (when the haplotype is not obtained from both partitions, immediately goes to next k). The ligating unit 102h counts the number of haplotypes in each partition to execute an l iteration and an m iteration up to the number of times as many as the number of haplotypes. The l iteration first initializes l to 1, increments l by one for each iteration, and repeats this as long as "l<=the number of haplotypes with the copy number k in the partition j". The m iteration first initializes m to 1, increments 1 by one for each iteration, and repeats this as long as "m<=the number of haplotypes with the copy number k in the partition j+1". In the iteration, as explained above in the embodiment, the haplotypes having the same number of copy units are ligated, without the copy unit left over, to create all possible new haplotypes.

That is to say, the ligating unit 102h regards a haplotype m as a vector having elements, which are the copy units, and obtains all permutation vectors (SF-52). The permutation vector means the vector obtained by permutationally changing the elements. All the permutation vectors are obtained in order to create all possible new haplotypes. The ligating unit 102h regards the haplotype l as the vector having elements, which are the copy units, and performs a vectoral character string binding between a copy unit of a haplotype l and a copy unit in each permutation vector obtained above to obtain a new character string vector (SF-52). The vectoral character string binding is to regard the copy unit as the character string and to bind one character string with another independently in each element, as explained above in the embodiment. The character string vector thus obtained is next regarded as a character string set (without order relationship) (there is no order relationship in the copy unit in the haplotype in this embodiment). In this manner, the obtained character string set becomes the ligated haplotype (SF-53). The m and l iterations are terminated. In this manner, all possible haplotypes are created by ligating all the copy units for each copy number.

After terminating the k iteration, the ligating unit 102h makes the ligated haplotypes unique (same, redundant haplotypes are eliminated) (SF-54).

The haplotype estimating apparatus 100 enters the iteration for each count number pattern. That is to say, the ligating unit 102h creates the diplotype in pairs in every combination from the ligated haplotypes (SF-55), under condition that a total copy number of the count number pattern $c_k$ is equal to the sum of the copy numbers of two haplotypes. The total copy number means the maximum number (across p) of the total count number $\Sigma nc_k(M_p, F_n)$ (n=1, 2, 3, . . . ; p=1, 2, 3, . . . ) and is calculated by the maximum value-calculating unit 102a before the partitioning (that is to say, before the process at SF-2). For example, when the total copy number is 3, the diplotype is created from two haplotypes of which copy numbers are 0 and 3, or from two haplotypes of which copy numbers are 1 and 2. The ligating unit 102h selects only the diplotypes consistent with the count number data in the partition obtained by combining the partition j and the partition j+1 from all the created diplotypes (SF-56).

Returning again to the explanation in FIG. 20, the ligating unit 102h performs the calculation of the haplotype frequency by the EM algorithm by the process of the haplotype frequency-calculating unit 102f in the partition obtained by combining the partition j and the partition j+1 (SF-6). That is to say, the haplotype frequency-calculating unit 102f calculates the haplotype frequency by executing the M step and the E step using the count number data in the partition obtained by combining the partition j and the partition j+1 and the diplotype obtained at SF-5. At the same time, the haplotype frequency-calculating unit 102f records the accumulated average frequency of each haplotype.

The haplotype estimating apparatus 100 outputs the haplotypes and the frequencies thereof to the result file after terminating the i iteration (SF-7).

Demonstration of PL Strategy by Simulation

A simulation experiment is performed in order to confirm whether the same result (the haplotypes of the copy number polymorphism and the frequencies thereof) can be estimated and the calculation process can be shortened by the PL strategy by the processes of the partitioning unit 102g and the ligating unit 102h by the above-explained example. That is to say, in the following simulation experiment, the haplotype estimating apparatus 100 performs two types of haplotype estimation processes of the cases in which the partition process and the ligation process are performed and in which the processes are not performed, and it is verified whether the haplotype estimation result by the PL strategy is similar to that in the case in which the partition and ligation processes are not performed, and whether the calculation speed can be improved. FIG. 22 is an illustration of an example of the haplotypes and the frequencies thereof used in the simulation experiment. FIG. 23 is count number data of the 500 individuals created from the read haplotypes and the probabilities thereof.

In this example, it was tested whether the haplotypes and the probabilities thereof shown in FIG. 22 can be estimated by the PL strategy in a short time only from the count number data in FIG. 23. For comparison, it was performed by a brute force method (the same method in the example of the above-explained EM algorithm) without using the PL strategy. The setting of the EM algorithm used in the brute force method and the PL strategy was set the same as the setting of the above-explained example. In the PL strategy, the marker sites (M) were partitioned every adjacent four marker sites. The frequency of the haplotype to be eliminated in the partition was set equal to or smaller than $10^{-5}$. The haplotype buffer size was set to 50.

As a result of application of this example, a result as shown in FIG. 24 was obtained. In the result, the calculation times and the estimated frequencies of the haplotypes in the brute force method and the PL strategy are indicated. The estimated frequencies are substantially the same in the brute force method and in the PL strategy, and they are closer to a correct answer in FIG. 22. That is to say, all the frequencies of the haplotypes present in FIG. 24 but not present in FIG. 22 are low, all the haplotypes present in FIG. 22 appear in FIG. 24, and the estimated frequencies thereof are substantially the same as the correct frequencies. The calculation time in the PL strategy is significantly shorter than that in the brute force method. Therefore, it was verified that the haplotypes of the CNP and the frequencies thereof can be estimated in a shorter time by the PL strategy of the present invention.

Demonstration of Second Embodiment Handling Number of Copy Unit by Simulation

An example to which the second embodiment using the total summation of the copy numbers of the copy number polymorphism in each individual is applied is explained with reference to FIGS. 25 to 30.

In this example to which the above-explained second embodiment is applied, the simulation experiment is performed in order to confirm whether the haplotypes of the copy number polymorphism and the frequencies thereof can be estimated from the count number data using the summation of the copy numbers of the copy number polymorphism. That is to say, in this example, the copy number summation data in the individual is created based on the preset probabilities (frequencies) of the haplotypes of the copy number polymorphism in the group set. The process according to the second embodiment was executed based on the copy number summation data to perform the test whether it is possible to estimate the original probabilities (frequencies) of the haplotypes. FIG. 25 is an illustration of the copy numbers (the number of copy units) present in the haplotypes and the probabilities of the haplotypes set in this example. FIG. 26 is an illustration representing the copy numbers shown in FIG. 25 as the count numbers of the provisional nucleotide $F_1$.

That is to say, as the setting of the simulation experiment, as shown in FIG. 25, the probabilities of cases in which the copy numbers of the haplotypes are 0, 1, 2, and 3, were set 0.25. The copy number is treated as the count number of the provisional nucleotide $F_1$ in the process of the second embodiment as shown in FIG. 26.

Based on the set probabilities, combinations of the copy numbers of the haplotypes for 500 individuals are arbitrarily extracted and summation of the copy numbers (summation of the copy numbers across the two homologous chromosomes) was stored in the copy number summation file 106d. FIG. 27 is an illustration of the summation of the copy numbers in each individual drawn. FIG. 28 is an illustration representing the summation of the copy numbers shown in FIG. 27 as the count numbers of the provisional nucleotide $F_1$.

Subsequently, it was tested whether the haplotype estimating apparatus 100 can estimate the probabilities (frequencies) of the haplotypes as shown in FIG. 25 using the copy number summation data shown in FIG. 27. That is to say, the count number table-creating unit 102j first created the count number table in which the summation of the copy numbers stored in the copy number summation file 106d as shown in FIG. 27 is set to the count number of the provisional nucleotide $F_1$ as shown in FIG. 28.

The haplotype estimating apparatus 100 executed a subsequent haplotype estimation process to estimate the haplotypes and the frequencies thereof. When executing the haplotype estimation process, the settings of the EM algorithm are the same as those of the above explanation. FIG. 29 is an illustration of the haplotype character strings and the frequencies thereof estimated by the haplotype estimating apparatus 100. FIG. 30 is an illustration of the haplotypes of each copy number and the frequencies thereof calculated from the estimated haplotype character strings.

The copy number-setting unit 102k calculated the number of the polymorphic identification characters ($F_1$) associated with the provisional nucleotide in the haplotype character strings in the haplotypes estimated as FIG. 29, and set the calculated number as shown in FIG. 30 as the copy number in the haplotype.

When comparing the set probabilities of the haplotypes shown in FIG. 25 with the estimated frequencies of the haplotypes, which is the estimation result shown in FIG. 30, the estimated frequencies (approximately 0.245 to 0.260) were substantially equivalent to the set probability 0.25 for the haplotype of which copy numbers are 0, 1, 2 and 3, on the other hand, the estimated frequencies were substantially 0 (1.05E-05 or smaller) for the haplotypes with 4, 5, and 6 copy numbers, of which the frequencies were set to 0. That is to say, the estimated frequency is substantially equal to the correct frequency (set probability), and it was verified that the number of copy units present in the haplotype and the frequency of the haplotype can be estimated only from the copy number summation data. This is the end of the explanation of the verification simulation according to the second embodiment by the number of the copy units.

Other Embodiments

The embodiments of the present invention have been described above. However, the present invention may be executed in not only the embodiment described above but also various different embodiments within the technical idea described in the scope of the invention.

In the above embodiments, an example in which the haplotype estimating apparatus 100 mainly performs the processes in a standalone mode is explained. However, as described in the embodiments, a process may be performed in response to a request from another terminal apparatus constituted by a housing different from that of the haplotype estimating apparatus 100, and the process result may be returned to the client terminal.

Of each of the processes explained in the embodiments, all or some processes explained to be automatically performed may be manually performed. Alternatively, all or some processes explained to be manually performed may also be automatically performed by a known method.

In addition, the procedures, the control procedures, the specific names, the information including parameters such as registered data, and the database configurations which are described in the literatures or the drawings may be arbitrarily changed unless otherwise noted.

With respect to the haplotype estimating apparatus 100, the constituent elements shown in the drawings are functionally schematic. The constituent elements need not be always physically arranged as shown in the drawings.

For example, all or some processing functions of the devices in the haplotype estimating apparatus 100, in particular, processing functions performed by the control unit 102 may be realized by a central processing unit (CPU) and a program interpreted and executed by the CPU or may also be realized by hardware realized by a wired logic. The program is recorded on a recording medium (will be described later) and mechanically read by the haplotype estimating apparatus 100 as needed. More specifically, on the storage unit 106 such as a ROM or an HD, a computer program which gives an instruction to the CPU in cooperation with an operating system (OS) to perform various process is recorded. The computer program is executed by being loaded on a RAM, and constitutes a control unit in cooperation with the CPU.

The computer program may be stored in an application program server connected to the haplotype estimating apparatus 100 through an arbitrary network 300. The computer program in whole or in part may be downloaded as needed.

A program which causes a computer to execute a method according to the present invention may also be stored in a computer readable recording medium. In this case, the "recording medium" includes an arbitrary "portable physical medium" such as a flexible disk, a magnet-optical disk, a ROM, an EPROM, an EEPROM, a CD-ROM, an MO, or a DVD or a "communication medium" such as a communication line or a carrier wave which holds a program for a short period of time when the program is transmitted through a network typified by a LAN, a WAN, and the Internet.

The "program" is a data processing method described in an arbitrary language or a describing method. As a format of the "program", any format such as a source code or a binary code may be used. The "program" is not always singularly constructed, and includes a program obtained by distributing and arranging multiple modules or libraries or a program that achieves the function in cooperation with another program typified by an operating system (OS). In the apparatuses according to the embodiments, as a specific configuration to read a recording medium, a read procedure, an install procedure used after the reading, and the like, known configurations and procedures may be used.

Various databases or the like (count number table 106a to copy number summation file 106d) stored in the storage unit 106 are a memory device such as a RAM or a ROM, a fixed disk device such as a hard disk drive, and a storage unit such as a flexible disk or an optical disk and store various programs, tables, databases, Web page files used in various processes or Web site provision.

The haplotype estimating apparatus 100 may be realized by connecting a known information processing apparatus such as a personal computer or a workstation and installing software (including a program, data, or the like) which causes the information processing apparatus to realize the method according to the present invention.

Furthermore, a specific configuration of distribution and integration of the devices is not limited to that shown in the drawings. All or some devices can be configured such that the devices are functionally or physically distributed and integrated in arbitrary units depending on various additions.

Industrial Applicability

As described above in detail, according to the present invention, a haplotype estimating apparatus, a haplotype estimating method, and a program that estimate a haplotype and a frequency thereof with high accuracy from experimental data regarding a copy number polymorphism in consideration of a nucleotide polymorphism can be provided. For this reason, the present invention can be used in various fields such as medical care and biotechnology.

The invention claimed is:

1. A haplotype estimating apparatus that estimates a haplotype from genotype data including a copy number polymorphism and a nucleotide polymorphism of each individual in a group, the haplotype estimating apparatus comprising:
a processor; and
a storage unit,
wherein the storage unit includes a count number table that stores count numbers obtained by counting polymorphic nucleotides associated with marker sites specified by a label on a copy unit of the copy number polymorphism using the genotype data for each individual, for each type of the polymorphic nucleotides, and
wherein the processor is programmed to:
calculate, by a maximum value-calculating unit, a sum of the count numbers for each of the marker sites based on the count numbers of the individual stored in the count number table to obtain a maximum value of the sum of the count numbers;
enumerate, by a polymorphic identification character-enumerating unit, polymorphic identification characters associated with the type of the polymorphic nucleotides up to the number as many as the count numbers of the polymorphic nucleotides;
permutate, by a character string-creating unit, the enumerated polymorphic identification characters so as to create any character string that has copy units of which the number equals the maximum value;
divide, by a haplotype character string-storing unit, the character string created by the character string-creating unit into two by the copy unit to store the divided strings as a combination of the haplotype character strings; and
calculate, by a haplotype-estimating unit, the number of identical haplotype character strings in the group, obtain a frequency of the haplotype character string in the group, and estimate the combination of the haplotype character strings of each individual of which frequency satisfying a predetermined condition as the combination of the haplotypes.

2. The haplotype estimating apparatus according to claim 1, wherein the processor is further programmed to calculate, by the haplotype-estimating unit, the frequency of the haplotype character string based on the Hardy-Weinberg Principle, and use a Hardy-Weinberg equilibrium in the group as the predetermined condition.

3. The haplotype estimating apparatus according to claim 1, wherein the processor is further programmed to enumerate, by the polymorphic identification character-enumerating unit, the polymorphic identification character indicating a nucleotide deletion as a type of the polymorphic nucleotide up to the number as many as the number obtained by subtracting the sum from the maximum value.

4. The haplotype estimating apparatus according to claim 1, wherein the processor is further programmed to confirm, by the character string-creating unit, that the number of the polymorphic identification characters in the created character string and the count number of the polymorphic nucleotide for each type in the count number table that conform to each other, and eliminate the character string when they do not conform to each other.

5. The haplotype estimating apparatus according to claim 1, wherein the processor is further programmed to:
partition, by a partitioning unit, the copy unit into multiple partitions by a unit of the marker sites, and, for the nucleotide polymorphism of the marker sites included in the partition, control the maximum value-calculating unit, the polymorphic identification character-enumerating unit, the character string-creating unit, the haplotype character string-storing unit, and the haplotype-estimating unit to execute the process for each of the partitions; and
reproduce, by a ligating unit, the haplotype character string composed of the partitions by ligating each of the partitions on the copy unit with each other between the haplotype character strings having a same repeated pattern of the copy unit, for the haplotype character string estimated by the haplotype-estimating unit for each of the partitions.

6. A computer program that is tangibly embodied on a non-transitory computer-readable storage medium that causes a processor to estimate a haplotype from genotype data including a copy number polymorphism and a nucleotide polymorphism of each individual in a group, wherein a haplotype estimating apparatus includes the processor and a storage unit, wherein the storage unit includes a count number table that stores count numbers obtained by counting polymorphic nucleotides associated with marker sites specified by a label on a copy unit of the copy number polymorphism using the genotype data for each individual, for each type of the polymorphic nucleotides, and wherein the computer program causes the processor to execute steps of:
calculating a sum of the count numbers for each of the marker sites based on the count numbers of the individual stored in the count number table to obtain a maximum value of the sum of the count numbers;
enumerating polymorphic identification characters associated with the type of the polymorphic nucleotides up to the number as many as the count numbers of the polymorphic nucleotides;

permutating the enumerated polymorphic identification characters so as to create any character string that has copy units of which the number equals the maximum value;

dividing the character string created at the character string creating step into two by the copy unit to store the divided strings as a combination of the haplotype character strings; and calculating the number of identical haplotype character strings in the group, obtaining a frequency of the haplotype character string in the group, and estimating the combination of the haplotype character strings of each individual of which frequency satisfying a predetermined condition as the combination of the haplotypes.

* * * * *